(12) United States Patent
Ushio et al.

(10) Patent No.: US 6,191,289 B1
(45) Date of Patent: *Feb. 20, 2001

(54) PRODUCTION PROCESS AND INTERMEDIATE OF TETRAZOLE COMPOUND

(75) Inventors: Hideki Ushio, Takatsuki; Takayuki Higashii, Yokohama; Masayoshi Minai, Moriyama; Akihiko Nakamura, Takatsuki, all of (JP)

(73) Assignee: Sumitomo Chemical Company, Limited, Osaka (JP)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/176,198

(22) Filed: Oct. 21, 1998

Related U.S. Application Data

(62) Division of application No. 08/592,375, filed as application No. PCT/JP95/00919 on May 15, 1995.

(30) Foreign Application Priority Data

May 16, 1994 (JP) .................................................. 5-100832
Mar. 28, 1995 (JP) .................................................. 6-069204

(51) Int. Cl.$^7$ .................................................. C07D 257/04
(52) U.S. Cl. .................................................. 549/402; 548/252
(58) Field of Search .................................................. 548/253, 252

(56) References Cited

U.S. PATENT DOCUMENTS

| 3,694,450 | 9/1972 | Wei . |
| 4,544,759 | 10/1985 | Hlavka et al. . |
| 5,124,324 | 6/1992 | Kedersky . |
| 5,278,312 | 1/1994 | Chekroun et al. . |
| 5,310,928 | 5/1994 | Lo et al. . |

FOREIGN PATENT DOCUMENTS

| 0291969A2 | 11/1988 | (EP) . |
| 0606065A1 | 7/1994 | (EP) . |
| 2184829A | 7/1990 | (JP) . |
| 53310709A | 11/1993 | (JP) . |
| 72805A | 1/1995 | (JP) . |
| WO 94/12492A1 | 6/1994 | (WO) . |

OTHER PUBLICATIONS

ALdrich Catalog pp. 802–803, 1996.*
Brown et al., *J. Am. Chem. Soc.*, vol. 82, pp. 4700–4703 (1960).
Ellis, *Journal of Medicinal Chemistry*, vol. 15, No. 8, pp. 865–867 (1972).
Chemical Abstracts, 85:177373e, p. 521 (Dec. 1976).
Huff et al., *Tetrahedron Letters*, vol. 34, No. 50, pp. 8011–8014 (1993).
Russell et al., *J. Org. Chem.*, vol. 58, pp. 5023–5024 (1993).
Wittenberger et al., *J. Org. Chem.*, vol. 58, pp. 4139–4141 (1993).
Duncia et al., *J. Org. Chem.*, vol. 56, pp. 2395–2400 (1991).
Doyle et al., *Synthesis*, pp. 583–584 (Aug. 1974).
Van der Burg., *Rec. Trav. Chim.*, vol. 74, pp. 257–262 (1955).
Kauffmann et al., *Chem. Ber.*, vol. 97, pp. 3436–3443 (1964).
Pierce et al., *J. Org. Chem.*, vol. 58, pp. 4642–4645 (1993).
Stanovnik, Synthesis (10) 807–10, Oct. 1986.*
Ellis J. Med. Chem. 15(8) 865–7, Aug. 1972.*
Decroix et al., *Bulletin de la Societe Chimique de France*, Synthesis of Polynitrogen Compounds from Furanic, Thiophenic or Selenophenic Nitriles or Iminoethers, No. 3–4, pp. 621–627 (1976) (w/translation).
Neilson et al., *Chemical Reviews*, vol. 70, pp. 151–170 (1970).
Doelling, K.; Zaschke, H.; Schubert, H.; Liquid–crystal thiazoles; Sekt. Chem., Martin–Luther–Univ. Halle–Wittenberg, Halle/Saale; J. Prakt. Chem. (1979), 321(4), 643–54.

* cited by examiner

Primary Examiner—Robert Gerstl
(74) Attorney, Agent, or Firm—Birch, Stewart, Kolasch & Birch, LLP

(57) ABSTRACT

There are disclosed an industrially favorable process for producing a tetrazole compound of general formula (1):

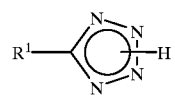

(1)

characterized in that a nitrile of general formula (2):

$$R^1CN \tag{2}$$

is reacted with hydrazine or a salt thereof in the presence of a catalyst, followed by reaction with a nitrous acid compound of general formula (3):

$$ANO_2 \tag{3}$$

or a nitrile of general formula (2) is reacted with hydrogen sulfide, followed by reaction with an alkyl halide of general formula (4):

$$R^4J \tag{4}$$

with hydrazine or a salt thereof, and then with a nitrous acid compound of general formula (3); and an intermediate of general formula (5):

$$R^1C(=R^5)R^6 \tag{5}$$

which is useful for the production of the tetrazole compound (in which $R^1$ to $R^6$, A and J in the above formulas are as defined in the specification).

10 Claims, No Drawings

PRODUCTION PROCESS AND INTERMEDIATE OF TETRAZOLE COMPOUND

This application is a divisional of copending application Ser. No. 08/592,375, filed on Feb. 8, 1996. Application Ser. No. 08/592,375 is the national phase of PCT International Application No. PCT/JP95/00919 filed on May 15, 1995 under 35 U.S.C. § 371. The entire contents of each of the above identified applications are hereby incorporated by reference.

DESCRIPTION

1. Industrial Field for Utilization

The present invention relates to production processes and intermediates of tetrazole compounds. More particularly, it relates to 2-(tetrazol-5-yl)-4-oxo-4H-benzopyran derivatives which are known to be pharmacologically useful from the viewpoint of their antagonistic action to leukotrienes such as leukotrienes C and D, and it also relates to 2-(tetrazol-5-yl)-1,1'-biphenyl derivatives which are known to be pharmacologically useful from the viewpoint of their antagonistic action to angiotensin II. Further, it relates to processes for producing 5-phenyltetrazole derivatives which are useful as intermediates of the biphenyl derivatives, and it also relates to intermediates which are useful in their production.

2. Prior Art

As the process for producing tetrazole compounds such as 2-(tetrazol-5-yl)-4-oxo-4H-benzopyran derivatives, 2-(tetrazol-5-yl)-1,1'-biphenyl derivative and 5-phenyltetrazole derivatives, there has been known a process with an azide such as sodium azide, trialkyl tin azide or trimethylsilyl azide.

However, since azides are reacted with water or acids to produce hydrogen azide having toxic and explosive properties, the concentration of hydrogen azide in the gas phase in the upper part of a reactor should be strictly controlled during the reaction. It has been known that azides are liable to form an explosive salt with heavy metals. Therefore, the application of such a process with an azide on an industrial scale is disadvantageous from the viewpoint of its safety. Further, tin reagents such as trialkyl tin azide have drawbacks that they require a complicated procedure for the isolation of a product because of its lipophilicity and that tin-containing waste matters are formed in large quantities.

As the process for producing 2-(tetrazol-5-yl)-1,1'-biphenyl derivatives or 5-phenyltetrazole derivatives, another process is described in J. Org. Chem., 1991, 56, pp. 2395–2400, in which process biphenylcarboxylic acids or phenylcarboxylic acids are converted into their amides with cyanoethylamine, followed by chlorination with phosphorous pentachloride, and reaction with hydrazine and then with dinitrogen tetroxide gas.

This process, however, has disadvantages that the yield of a desired product is not satisfactory, that the step of deprotecting a cyanoethyl group used as a protecting group is needed, and that the production on an industrial scale finds difficulty in using phosphorous pentachloride.

OBJECTS OF THE INVENTION

It is an object of the present invention to provide a process for producing tetrazole compounds with safety in an industrially favorable manner.

It is another object of the present invention to provide intermediates useful for the production of the tetrazole compounds.

These and other objects and excellent advantages will be understood from the following description.

SUMMARY OF THE INVENTION

The present inventors have intensively studied on a process for producing tetrazole compounds. As a result, they have found that the above problems can be solved and the desired products can be obtained with safety in an industrially favorable manner by a process through amidrazone compounds with nitrile compounds as the starting materials, and they have made further studies, thereby completing the present invention.

Thus, the present invention provides:

[1] a process for producing a tetrazole compound of general formula (1):

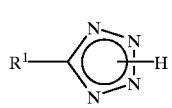
(1)

wherein $R^1$ is as defined below, characterized in that a nitrile of general formula (2):

$$R^1CN \tag{2}$$

wherein $R^1$ is a 4-oxo-4H-benzopyranyl group optionally substituted with $R^2$ or a phenyl group optionally substituted with X, in which $R^2$ is a hydroxy group, a halogen atom, an $R^3CONH$ group, a nitro group, a $C_1$–$C_5$ alkyl or $C_1$–$C_5$ alkoxy group; $R^3$ is a $C_1$–$C_{20}$ alkyl group, a phenyl group, a phenyl-substituted ($C_1$–$C_{20}$) alkyl group, a phenyl-substituted ($C_1$–$C_{20}$) alkoxyphenyl group or a ($C_1$–$C_{20}$) alkoxyphenyl group; X is a halogen atom, a phenyl group optionally substituted with Y, a $C_1$–$C_{20}$ alkyl group, a phenyl-substituted ($C_1$–$C_{20}$) alkyl group, a phenyl-substituted ($C_1$–$C_{20}$) alkoxy group or a $C_1$–$C_{20}$ alkoxy group; and Y is a $C_1$–$C_{20}$ alkyl group, a $C_1$–$C_{20}$ alkyl group substituted with one or more hydroxy groups with at least one hydrogen atom in the hydroxy group being optionally replaced for protection, a $C_1$–$C_{20}$ alkyl group substituted with one or more amino groups with at least one hydrogen atom in the amino group being optionally replaced for protection, a $C_1$–$C_{20}$ alkyl group with at least one hydrogen atom being replaced by a halogen atom, a $C_1$–$C_{20}$ alkoxy group, a $C_1$–$C_{20}$ alkoxy group substituted with one or more hydroxy groups with at least one hydrogen atom in the hydroxy group being optionally replaced for protection, a $C_1$–$C_{20}$ alkoxy group substituted with one or more amino groups with at least one hydrogen atom in the amino group being optionally replaced for protection, or a $C_1$–$C_{20}$ alkoxy group with at least one hydrogen atom being replaced by a halogen atom, is reacted with hydrazine or a salt thereof in the presence of a catalyst, followed by reaction with a nitrous acid compound of general formula (3):

$$ANO_2 \tag{3}$$

wherein A is a hydrogen atom, an alkyl metal, an alkaline earth metal or a $C_1$–$C_{20}$ alkyl group;

[2] a process for producing tetrazole compound (1), characterized in that nitrile (2) is reacted with hydrogen sulfide, followed by reaction with an alkyl halide of general formula (4):

$$R^4J \tag{4}$$

wherein $R^4$ is a $C_1$–$C_{20}$ alkyl group and J is a halogen atom, with hydrazine or a salt thereof, and then with nitrous acid compound (3); and

[3] an amide of general formula (5):

$$R^1C(=R^5)R^6 \qquad (5)$$

wherein $R^1$ is as defined above; $R^5$ is a sulfur atom or an NH group; and $R^6$ is an $NH_2$ group, an $SR^4$ group or an $NHNH_2$ group, in which when $R^5$ is a sulfur atom, then $R^6$ is an $NH_2$ group, and when $R^5$ is an NH group, then $R^6$ is an $SR^4$ group or an $NHNH_2$ group; and $R^4$ is as defined above.

DETAILED DESCRIPTION OF THE INVENTION

As the $R^1$ in the nitrile (2) used in the present invention, there can be mentioned 4-oxo-4H-benzopyranyl groups optionally substituted with $R^2$ or phenyl groups optionally substituted with X.

As the $R^2$, there can be mentioned hydroxy group; halogen atoms such as fluorine, chlorine, bromine and iodine atoms; $R^3$CONH groups; nitro group; straight chain or branched $C_1$–$C_5$ alkyl groups such as methyl, ethyl, propyl, butyl and pentyl groups; and straight chain or branched $C_1$–$C_5$ alkoxy groups such as methoxy, ethoxy, propoxy, butoxy and pentoxy groups.

As the $R^3$, there can be mentioned straight chain or branched $C_1$–$C_{20}$, preferably $C_1$–$C_{10}$, and more preferably $C_1$–$C_5$, alkyl groups such as methyl, ethyl, propyl, butyl, pentyl, octyl, decyl, pentadecyl and octadecyl groups; phenyl group; straight chain or branched $C_1$–$C_{20}$, preferably $C_1$–$C_{10}$, and more preferably $C_1$–$C_5$, alkyl groups with one of the hydrogen atoms being replaced by a phenyl group, such as benzyl, phenethyl, phenylpropyl, phenylbutyl, phenyloctyl, phenylpentadecyl and 1-phenylethyl groups; straight chain or branched ($C_1$–$C_{20}$, preferably $C_1$–$C_{10}$, and more preferably $C_1$–$C_5$) alkoxyphenyl groups with one of the hydrogen atoms in the alkoxy group being replaced by a phenyl group, such as benzyloxyphenyl, phenethyloxyphenyl, phenylpropyloxyphenyl, 4-phenylbutoxyphenyl, 3-phenylbutoxyphenyl, phenylpentadecyloxyphenyl and 1-phenylethoxyphenyl groups; and straight chain or branched ($C_1$–$C_{20}$, preferably $C_1$–$C_{10}$, and more preferably $C_1$–$C_5$) alkoxyphenyl groups such as methoxyphenyl, ethoxyphenyl, propoxyphenyl, butoxyphenyl, octyloxyphenyl, penta-decyloxyphenyl, octadecyloxyphenyl, 1,1-dimethylmethoxyphenyl and 1,1,1-trimethylmethoxyphenyl groups.

As the X, there can be mentioned halogen atoms; phenyl groups optionally substituted with Y; straight chain or branched $C_1$–$C_{20}$, preferably $C_1$–$C_{10}$, and more preferably $C_1$–$C_5$, alkyl groups such as methyl, ethyl, propyl, butyl, pentyl, octyl, decyl, pentadecyl and octadecyl groups; straight chain or branched $C_1$–$C_{20}$, preferably $C_1$–$C_{10}$, and more preferably $C_1$–$C_5$, alkyl groups with one of the hydrogen atoms being replaced by a phenyl group, such as benzyl, phenethyl, phenylpropyl, phenylbutyl, phenyloctyl, phenylpentadecyl and 3-phenyl-2-methylpropionyl groups; straight chain or branched $C_1$–$C_{20}$, preferably $C_1$–$C_{10}$, and more preferably $C_1$–$C_5$, alkoxy groups with one of the hydrogen atoms in the alkoxy group being replaced by a phenyl group, such as benzyloxy, phenethyloxy, phenylpropyloxy, 4-phenylbutoxy, 3-phenylbutoxy, phenylpentadecyloxy and 1-phenylethoxy groups; and straight chain or branched $C_1$–$C_{20}$, preferably $C_1$–$C_{10}$, and more preferably $C_1$–$C_5$, alkoxy groups such as methoxy, ethoxy, propoxy, butoxy, pentoxy, octyloxy, decyloxy, pentadecyloxy and octadecyloxy groups.

As the Y, there can be mentioned straight chain or branched $C_1$–$C_{20}$, preferably $C_1$–$C_{10}$, and more preferably $C_1$–$C_5$, alkyl groups such as methyl, ethyl, propyl, butyl, pentyl, octyl, decyl, pentadecyl and octadecyl groups; straight chain or branched $C_1$–$C_{20}$, preferably $C_1$–$C_{10}$; and more preferably $C_1$–$C_5$, alkyl groups substituted with one or more hydroxy groups with at least one hydrogen atom in the hydroxy group being optionally replaced for protection, such as hydroxymethyl, hydroxyethyl, hydroxypropyl, hydroxybutyl, hydroxypentyl, hydroxyoctyl, hydroxydecyl, hydroxypentadecyl and hydroxyoctadecyl groups, and these groups with the hydroxy group being protected by a protecting group; straight chain or branched $C_1$–$C_{20}$, preferably $C_1$–$C_{10}$, and more preferably $C_1$–$C_5$, alkyl groups substituted with one or more amino groups with at least one hydrogen atom in the amino group being optionally replaced for protection, such as aminomethyl, aminoethyl, aminopropyl, aminobutyl, aminopentyl, aminooctyl, aminodecyl, aminopentadecyl and aminooctadecyl groups, and these groups with the amino group being protected by a protecting group; straight chain or branched $C_1$–$C_{20}$, preferably $C_1$–$C_{10}$, and more preferably $C_1$–$C_5$, alkyl groups with at least one hydrogen atom being replaced by a halogen atom, such as chloromethyl, fluoromethyl, bromomethyl, iodomethyl, chloroethyl, fluoroethyl, bromoethyl, iodoethyl, bromononyl, bromooctadecyl, dichloromethyl, dibromomethyl and trichloromethyl groups; straight chain or branched $C_1$–$C_{20}$, preferably $C_1$–$C_{10}$, and more preferably $C_1$–$C_5$, alkoxy groups such as methoxy, ethoxy, propyloxy, butoxy, pentoxy, octyloxy, decyloxy, pentadecyloxy and octadecyloxy groups; straight chain or branched $C_1$–$C_{20}$, preferably $C_1$–$C_{10}$, and more preferably $C_1$–$C_5$, alkoxy groups substituted with one or more hydroxy groups with at least one hydrogen atom in the hydroxy group being optionally replaced for protection, such as hydroxymethoxy, hydroxyethoxy, hydroxypropoxy, hydroxybutoxy, hydroxypentoxy, hydroxyoctyloxy, hydroxydecyloxy, hydroxypentadecyloxy and hydroxyoctadecyloxy groups, and these groups with the hydroxy group being protected by a protecting group; and straight chain or branched $C_1$–$C_{20}$, preferably $C_1$–$C_{10}$, and more preferably $C_1$–$C_5$, alkoxy groups with at least one hydrogen atom being replaced by a halogen atom, such as chloromethoxy, fluoromethoxy, bromomethoxy, iodomethoxy, chloroethoxy, fluoroethoxy, bromoethoxy, iodoethoxy, bromopentoxy, bromononyloxy and bromooctyloxy groups.

As the protecting group for hydroxy groups, there can be mentioned, for example, aliphatic acyl groups, typical examples of which are alkylcarbonyl, cycloalkylcarbonyl and aromatic carbonyl groups such as acetyl, propionyl, valeryl, adamantoyl and 2,4,6-trimethylbenzoyl groups; halogen atoms such as chlorine and bromine atoms; benzyl groups optionally substituted with an alkyl group such as methyl, ethyl, propyl or butyl group, or with an alkoxy group such as methoxy, ethoxy, propoxy or butoxy group; trialkylsilyl, dialkylphenylsilyl, alkyldiphenylsilyl, triphenylsilyl, aralkyldialkylsilyl, diaralkylalkylsilyl and triaralkylsilyl groups, and these groups with at least one hydrogen atom in the aralkyl or phenyl group being replaced by a halogen atom, an alkyl group, an alkoxy group or the like, such as trimethylsilyl, triethylsilyl, dimethylphenylsilyl, dimethylbenzylsilyl, methyldibenzylsilyl, tribenzylsilyl, dimethylbutylsilyl, methyldiphenylsilyl and triphenylsilyl groups; and alkoxyalkyl groups such as tetrahydropyranyl, tetrahydrofuranyl, ethoxyethyl and propoxyethyl groups.

As the protecting group for amino groups, there can be mentioned, for example, oxycarbonyl groups such as methoxycarbonyl, 2,2,2-trichloroethoxycarbonyl, 1,1- dimethyl-2-chloroethoxycarbonyl, cyclobutoxycarbonyl, 1-adamantyloxycarbonyl, 8-quinolyloxycarbonyl, benzyloxycarbonyl and tertiary-butoxycarbonyl groups; alkoxymethyl groups such as methoxymethyl group; phosphinyl groups such as N-diphenylphosphinyl and N-dimethylthiophosphinyl groups; sulfonyl groups such as 2,4,6-trimethylbenzenesulfonyl, toluenesulfonyl, trifluoromethylsulfonyl and methanesulfonyl groups. The amino group protected by a protecting group in the present invention further includes one or more nitrogen atoms constituting a nitrogen-containing heterocyclic ring such as imidazolyl, benzimidazolyl, purine, pyrimidine or triazole ring.

As the nitrile (2), there can be mentioned, for example, 4-oxo-4H-benzopyranyl group-containing nitriles such as 5-hydroxy-2-cyano-4-oxo-4H-benzopyran, 7-hydroxy-2-cyano-4-oxo-4H-benzopyran, 5,7-dihydroxy-2-cyano-4-oxo-4H-benzopyran, 5-methoxy-2-cyano-4-oxo-4H-benzopyran, 5-ethoxy-2-cyano-4-oxo-4H-benzopyran, 5-butoxy-2-cyano-4-oxo-4H-benzopyran, 5-pentoxy-2-cyano-4-oxo-4H-benzopyran, 6-chloro-2-cyano-4-oxo-4H-benzopyran, 2-cyano-4-oxo-4H-benzopyran, 8-acetylamino-2-cyano-4-oxo-4H-benzopyran, 6-acetylamino-2-cyano-4-oxo-4H-benzopyran, 8-propionylaamino-2-cyano-4-oxo-4H-benzopyran, 6-propionylamino-2-cyano-4-oxo-4H-benzopyran, 8-nonanoylamino-2-cyano-4-oxo-4H-benzopyran, 6-nonanoylamino-2-cyano-4-oxo-4H-benzopyran, 8-hexadecanoylamino-2-cyano-4-oxo-4H-benzopyran, 6-hexadecanoylamino-2-cyano-4-oxo4H-benzopyran, 8-benzoylamino-2-cyano-4-oxo-4H-benzopyran, 6-benzoylamino-2-cyano4-oxo-4H-benzopyran, 8-(3-phenylpropionyl)amino-2-cyano-4-oxo-4H-benzopyran, 6-(3-propionyl)amino-2-cyano-4-oxo-4H-benzopyran, 8-(9-phenylnonanoyl)amino-2-cyano-4-oxo-4H-benzopyran, 6-(9-phenylnonanoyl)amino-2-cyano-4-oxo-4H-benzopyran, 8-(16-phenylhexadecanoyl)amino-2-cyano-4-oxo-4H-benzopyran, 6-(16-phenylhexadecanoyl)amino-2-cyano-4-oxo-4H-benzopyran, 8-(4-methoxybenzoyl)amino-2-cyano-4-oxo-4H-benzopyran, 6-(4-methoxybenzoyl)amino-2-cyano-4-oxo-4H-benzopyran, 8-(4-ethoxybenzoyl)amino-2-cyano-4-oxo-4H-benzopyran, 6-(4-ethoxybenzoyl)amino-2-cyano-4-oxo-4H-benzopyran, 8-(4-propoxybenzoyl)amino-2-cyano-4-oxo-4H-benzopyran, 6-(4-propoxybenzoyl)amino-2-cyano-4-oxo-4H-benzopyran, 8-(4-butoxybenzoyl)amino-2-cyano-4-oxo-4H-benzopyran, 6-(4-butoxybenzoyl)amino-2-cyano-4-oxo-4H-benzopyran, 8-[4-(1,1-dimethylmethoxy)benzoyl]amino-2-cyano-4-oxo-4H-benzopyran, 6-[4-(1,1-dimethylmethoxy)benzoyl]amino-2-cyano-4-oxo-4H-benzopyran, 8-[4-(1,1,1-trimethylmethoxy)benzoyl]-amino-2-cyano-4-oxo-4H-benzopyran, 6-[4-(1,1,1-trimethylmethoxy)benzoyl]amino-2-cyano-4-oxo-4H-benzopyran, 8-(4-octyloxybenzoyl)amino-2-cyano-4-oxo-4H-benzopyran, 6-(4-octyloxybenzoyl)amino-2-cyano-4-oxo-4H-benzopyran, 8-(4-pentadecyloxybenzoyl)amino-2-cyano-4-oxo-4H-benzopyran, 6-(4-pentadecyloxybenzoyl)amino-2-cyano-4-oxo-4H-benzopyran, 8-[4-(3-phenylbutoxy)benzoyl]amino-2-cyano-4-oxo-4H-benzopyran, 6-[4-(3-phenylbutoxy)benzoyl]amino-2-cyano-4-oxo-4H-benzopyran, 8-[4-(4-phenylbutoxy)benzoyl]amino-2-cyano-4-oxo-4H-benzopyran, 6-[4-(4-phenylbutoxy)benzoyl]amino-2-cyano-4-oxo-4H-benzopyran, 8-[4-(8-phenyloctyloxy)benzoyl]amino-2-cyano-4-oxo-4H-benzopyran, 6-[4-(8-phenyloctyloxy)benzoyl]amino-2-cyano-4-oxo-4H-benzopyran, 8-nitro-2-cyano-4-oxo-4H-benzopyran, 6-nitro-2-cyano-4-oxo4H-benzopyran, 8-nitro-6-chloro-2-cyano-4-oxo-4H-benzopyran and 8-nitro--6-bromo-2-cyano-4-oxo-4H-benzopyran; and aryl group-containing nitriles such as benzonitrile, 2-chlorobenzonitrile, 3-chlorobenzonitrile, 4-chlorobenzonitrile, 2-bromobenzonitrile, 3-bromobenzonitrile, 4-bromobenzonitrile, 2-fluorobenzonitrile, 3-fluorobenzonitrile, 4-fluorobenzonitrile, 2-methylbenzonitrile, 3-methylbenzonitrile, 4-methylbenzonitrile, 2-ethylbenzonitrile, 3-ethylbenzonitrile, 4-ethylbenzonitrile, 2-propylbenzonitrile, 3-propylbenzonitrile, 4-propylbenzonitrile, 2-butylbenzonitrile, 3-butylbenzonitrile, 4-butylbenzonitrile, 2-octylbenzonitrile, 3-octylbenzonitrile, 4-octylbenzonitrile, 2-pentadecylbenzonitrile, 3-pentadecylbenzonitrile, 4-pentadecylbenzonitrile, 2-benzylbenzonitrile, 3-benzylbenzonitrile, 4-benzylbenzonitrile, 2-phenethylbenzonitrile, 3-phenethylbenzonitrile, 4-phenethylbenzonitrile, 2-(4-phenylbutyl)benzonitrile, 3-(4-phenylbutyl)benzonitrile, 4-(4-phenylbutyl)benzonitrile, 2-(8-phenyloctyl)benzonitrile, 3-(8-phenyloctyl)benzonitrile, 4-(8-phenyl octyl )benzonitrile, 2-(15-phenylpentadecyl)benzonitrile, 3-(15-phenylpentadecyl)benzonitrile, 4-(15-phenylpentadecyl)benzonitrile, 2-methoxybenzonitrile, 3-methoxybenzonitrile, 4-methoxybenzonitrile, 2-ethoxybenzonitrile, 3-ethoxybenzonitrile, 4-ethoxybenzonitrile, 2-propoxybenzonitrile, 3-propoxybenzonitrile, 4-propoxybenzonitrile, 2-butoxybenzonitrile, 3-butoxybenzonitrile, 4-butoxybenzonitrile, 2-octyloxybenzonitrile, 3-octyloxybenzonitrile, 4-octyloxybenzonitrile, 2-pentadecyloxybenzonitrile, 3-pentadecyloxybenzonitrile, 4-pentadecyloxybenzonitrile, 2-benzyloxybenzonitrile, 3-benzyloxybenzonitrile, 4-benzyloxybenzonitrile, 2-phenethyloxybenzonitrile, 3-phenethyloxybenzonitrile, 4-phenethyloxybenzonitrile, 2-(4-phenylbutoxy)benzonitrile, 3-(4-phenylbutoxy)benzonitrile, 4-(4-phenylbutoxy)benzonitrile, 2-(8-phenyloctyloxy)benzonitrile, 3-(8-phenyloctyloxy)benzonitrile, 4-(8-phenyloctyloxy)benzonitrile, 2-(15-phenylpentadecyloxy)benzonitrile, 3-(15-phenylpentadecyloxy)benzonitrile, 4-(15-phenylpentadecyloxy)benzonitrile, 2-(1-phenyl)ethoxybenzonitrile, 3-(1-phenyl)ethoxybenzonitrile, 4-(1-phenyl)ethoxybenzonitrile, 2-cyano-1,1'-biphenyl, 2-cyano-4'-methyl-1,1'-biphenyl, 2-cyano-4'-ethyl-1,1'-biphenyl, 2-cyano-4'-propyl-1,1'-biphenyl, 2-cyano-4'-butyl-1,1'-biphenyl, 2-cyano-4'-octyl-1,1'-biphenyl, 2-cyano-4'-decyl-1,1'-biphenyl, 2-cyano-4'-hydroxymethyl-1,1'-biphenyl, 2-cyano-4'-(2-hydroxy)ethyl-1,1'-biphenyl, 2-cyano-4'-(3-hydroxy)propyl-1,1'-biphenyl, 2-cyano-4'-(4-hydroxy)butyl-1,1'-biphenyl, 2-cyano-4'-(8-hydroxy)octyl-1,1'-biphenyl, 2-cyano-4'-methoxymethyl-1,1'-biphenyl, 2-cyano-4'-(2-methoxy)ethyl-1,1'-biphenyl, 2-cyano-4'-(3-methoxy)propyl-1,1'-biphenyl, 2-cyano-4'-(4-methoxy)butyl-1,1'-biphenyl, 2-cyano-4'-(8-methoxy)octyl-1,1'-biphenyl, 2-cyano-4'-benzyloxymethyl-1,1'-biphenyl, 2-cyano-4'-(2-benzyloxy)ethyl-1,1'-biphenyl, 2-cyano-4-(3-benzyloxy)propyl-1,1'-biphenyl, 2-cyano-4'-(4-benzyloxy)butyl-1,1'-biphenyl, 2-cyano-4'-(8-benzyloxy)octyl -1,1'-biphenyl, 2-cyano-4'-[2-(4-methoxybenzyloxy)ethyl]-1,1'-biphenyl, 2-cyano-4'-[3-(4-methoxybenzyloxy)propyl]-1,1'-biphenyl, 2-cyano-4'-[4-(4-methoxybenzyloxy)butyl]-1,1'-biphenyl, 2-cyano-4'-[8-(4-methoxybenzyloxy)octyl]-1,1'-biphenyl, 2-cyano-4'-aminomethyl-1,1'-biphenyl, 2-cyano-4'-(2-amino)ethyl-1,1'-biphenyl, 2-cyano-4'-(3-amino)propyl-1,1'-biphenyl, 2-cyano-4'-(4-amino)butyl-1,1'-biphenyl, 2-cyano-4'-(8-amino)octyl-1,1'-biphenyl, 2-cyano-4'-(N-mesylamino)methyl-1,1'-biphenyl, 2-cyano-4'-(2-mesylamino)ethyl-1,1'-biphenyl, 2-cyano-4'-(3-mesylamino)propyl-1,1'-biphenyl, 2-cyano-4'-(4-mesylamino)butyl-1,1'-biphenyl, 2-cyano-4'-(8-mesylamino)octyl-1,1'-biphenyl, 2-cyano-4'-(benzyloxycarbonylamino)methyl-1,1'-biphenyl, 2-cyano-4'-(2-benzyloxycarbonylamino)ethyl-1,1'-biphenyl, 2-cyano-4'-(3-benzyloxycarbonylamino)propyl-1,1'-biphenyl, 2-cyano-4'-(4-benzyloxycarbonylamino)butyl-1,1'-biphenyl, 2-cyano-4'-(8-benzyloxycarbonylamino)octyl-1,1'-biphenyl, 2-cyano-4'-(tertiary-butoxycarbonylamino)methyl-1,1'-biphenyl, 2-cyano-4'-(2-tertiary-butoxycarbonylamino)ethyl-1,1'-biphenyl, 2-cyano-4'-(3-tertiary-butoxycarbonylamino)propyl-1,1'-biphenyl, 2-cyano-4'-(4-tertiary-butoxycarbonylamino)butyl-1,1'-biphenyl, 2-cyano-4'-(8-tertiary-butoxycarbonylamino)octyl-1,1'-biphenyl, 2-cyano-4'-chloromethyl-1,1'-biphenyl, 2-cyano-4'-bromomethyl-1,1'-biphenyl, 2-cyano-4'-(2-bromo)ethyl-1,1'-biphenyl, 2-cyano-4'-(3-bromo)propyl-1,1'-biphenyl, 2-cyano-4'-(4-bromo)butyl-1,1'-biphenyl, 2-cyano-4'-(8-bromo)octyl-1,1'-biphenyl, 2-cyano-4'-dichloromethyl-1,1'-biphenyl, 2-cyano-4'-trichloromethyl-1,1'-biphenyl, 2-cyano-4'-dibromomethyl-1,1'-biphenyl, 2-cyano-4'-tribromomethyl-1,1'-biphenyl, 2-cyano-4'-methoxy-1,1'-biphenyl, 2-cyano-4'-ethoxy-1,1'-biphenyl, 2-cyano4'-propoxy-1,1'-biphenyl, 2-cyano4'-butoxy-1,1'-biphenyl, 2-cyano-4'-chloromethoxy-1,1'-biphenyl and 2-cyano-4'-(2-chloro)ethoxy-1,1'-biphenyl.

As the hydrazine or the salt thereof, which is used in the present invention, there can be mentioned anhydrous hydrazine, aqueous hydrazine, and hydrazine salts such as hydrazine hydrochloride and hydrazine sulfate.

As the nitrous acid compound (3) used in the present invention, there can be mentioned nitrous acid; alkali metal nitrites such as sodium nitrite and potassium nitrite, and alkaline earth metal nitrites such as barium nitrite; $C_1$–$C_{20}$, preferably $C_1$–$C_{10}$, and more preferably $C_1$–$C_5$, alkyl nitrites such as ethyl nitrite and isoamyl nitrite.

According to the production process of the present invention, tetrazole compound (1) can be produced by reacting, nitrile (2) with hydrazine or a salt thereof in the presence of a catalyst, followed by reaction with nitrous acid compound (3).

The reaction of nitrile (2) with hydrazine or a salt thereof in the presence of a catalyst can be effected as follows.

The reaction of nitrile (2) with hydrazine or a salt thereof in the presence of a catalyst makes it possible to obtain an amidrazone of general formula (6):

$$R^1C(=NH)NHNH_2 \quad (6)$$

wherein $R^1$ is as defined above, which corresponds to the amide (5) where $R^5$ is an NH group and $R^6$ is an $NHNH_2$ group as the production intermediate of the present invention. The amidrazone (6) is tautomerized into an isomerized amidrazone of general formula (9):

$$R^1C(=NNH_2)NH_2 \quad (9)$$

wherein $R^1$ is as defined above, which is a tautomer thereof. In the present invention, both are represented by the term "amidrazone (6)".

The amount of hydrazine or a salt thereof, which is to be used, is usually from 1 to 20 moles, relative to nitrile (2).

As the catalyst used in the above reaction, there can be mentioned those which enhance the reactivity of nitrile (2). For example, there can be mentioned alkoxides such as sodium methoxide and sodium ethoxide; alkali metals such as sodium and potassium; alkali metal amides such as sodium amide, lithium amide and sodium hydrazide; alkali metal or alkaline earth metal hydrides such as lithium hydride, sodium hydride and calcium hydride; sulfides or salts thereof, such as hydrogen sulfide, methylmercaptan, ethylmercaptan, butylmercaptan, sodium sulfide and ammonium sulfide; thiocyanates such as potassium thiocyanate; organic amines including pyridine compounds such as pyridine, picoline and 2-methyl-5-ethylpyridine, alkylamines such as triethylamine, methylamine and dimethylamine, aromatic amines such as dimethylaniline and dimethylaminopyridine, and diamines, typical examples of which are alkylenediamines such as tetramethylethylenediamine and aromatic diamines such as phenylenediamine; and phase transfer catalysts, typical examples of which are organic quaternary ammonium salts such as tetrabutylammonium bromide, benzyltriethylammonium chloride and cetylpyridinium chloride. These can be used alone or as a mixture of two or more kinds of catalysts. Particularly preferred are hydrogen sulfide; mixtures of hydrogen sulfide and alkylamines such as dimethylamine and triethylamine; and alkoxides derived from lower alcohols, such as sodium methoxide and sodium ethoxide. The amount of catalyst to be used, although it may vary with the kind of catalyst used, is usually from 0.001 to 5 moles, preferably from 0.01 to 5 moles, and more preferably from 0.1 to 5 moles, relative to nitrile (2).

The above reaction is usually effected in the presence of an organic solvent. As the solvent used, there can be mentioned those which are inert to hydrazine or salts thereof, for example, hydrocarbons such as benzene, toluene and hexane; halogenated hydrocarbons such as dichloromethane, dichloroethane and chlorobenzene; nitrated hydrocarbons such as nitrobenzene and nitromethane; ethers such as diethyl ether and tetrahydrofuran; amides such as dimethylformamide; and alcohols such as methanol and ethanol. These can be used alone or as a mixture of two or more kinds of solvents. The amount of solvent to be used, although it can be appropriately determined, is usually from 1 to 100 times as much as the weight of nitrile (2).

The method and order for the addition of nitrile (2) and hydrazine or a salt thereof are not particularly limited, and usually, hydrazine or a salt thereof may be added to a mixture of nitrile (2), a catalyst and a solvent.

The reaction temperature is usually from −78° to +150° C., preferably from −50° to +100° C. The completion of the reaction can be monitored by an analytical method such as liquid chromatography. Usually, the disappearance of nitride (2) can be considered as the end point of the reaction.

After completion of the reaction, amidrazone (6) can be isolated by an ordinary procedure such as extraction or filtration, or can be used in the next step without isolation. Alternatively, amidrazone (6) can be isolated as a stable onium salt by the addition of an acid such as concentrated hydrochloric acid or acetic acid to the reaction mixture, and then used in the next step. In this case, the amount of acid to be added is usually from 1 to 5 moles, relative to amidrazone (6), and the isolation can be usually carried out by filtration.

As the amidrazone (6) thus obtained, there can be mentioned, for example, 4-oxo-4H-benzopyranyl group-containing amidrazones such as (5-hydroxy-4-oxo-4H-benzopyran-2-yl)amidrazone, (7-hydroxy-4-oxo-4H-benzopyran-2-yl)amidrazone, (5,7-dihydroxy-4-oxo-4H-benzopyran-2-yl)amidrazone, (5-methoxy-4-oxo-4H- benzopyran-2-yl)amidrazone, (5-ethoxy-4-oxo-4H-benzopyran-2-yl)amidrazone, (5-butoxy-4-oxo-4H-benzopyran-2-yl)amidrazone, (5-pentoxy-4-oxo-4H-benzopyran-2-yl)amidrazone, (6-chloro-4-oxo-4H-benzopyran-2-yl)amidrazone, (4-oxo-4H-benzopyran-2-yl) amidrazone, (8-acetylamino-4-oxo-4H-benzopyran-2-yl)amidrazone, (6-acetylamino-4-oxo-4H-benzopyran-2-yl)amidrazone, (8-propionylamino-4-oxo-4H-benzopyran-2-yl)amidrazone, (6-propionylamino-4-oxo-4H-benzopyran-2-yl)amidrazone, (8-nonanoylamino-4-oxo-4H-benzopyran-2-yl)amidrazone, (6-nonanoylamino-4-oxo-4H-benzopyran-2-yl)-amidrazone, (8-hexadecanoylamino-4-oxo-4H-benzopyran-2-yl)amidrazone, (6-hexadecanoylamino-4-oxo-4H-benzopyran-2-yl)amidrazone, (8-benzoylamino-4-oxo-4H-benzopyran-2-yl)amidrazone, (6-benzoylamino-4-oxo-4H-benzopyran-2-yl)amidrazone, [8-(3-phenylpropionyl)amino-4-oxo-4H-benzopyran-2-yl]amidrazone, [6-(3-propionyl)amino-4-oxo-4H-benzopyran-2-yl]amidrazone, [8-(9-phenylnonanoyl)amino-4-oxo-4H-benzopyran-2-yl]amidrazone, [6-(9-phenylnonanoyl)amino-4-oxo-4H-benzopyran-2-yl]amidrazone, [8-(16-phenylhexadecanoyl) amino-4-oxo-4H-benzopyran-2-yl]amidrazone, [6-(16-phenylhexadecanoyl) amino-4-oxo-4H-benzopyran-2-yl]amidrazone, [8-(4-methoxybenzoyl)amino-4-oxo-4H-benzopyran-2-yl]amidrazone, [6-(4-methoxybenzoyl)amino-4-oxo-4H-benzopyran-2-yl]amidrazone, [8-(4-ethoxybenzoyl)amino-4-oxo-4H-benzopyran-2-yl]amidrazone, [6-(4-ethoxybenzoyl)amino-4-oxo-4H-benzopyran-2-yl]-amidrazone, [8-(4-propoxybenzoyl)amino-4-oxo-4H-benzopyran-2-yl]amidrazone, [6-(4-propoxybenzoyl)amino-4-oxo-4H-benzopyran-2-yl]amidrazone, [8-(4-butoxybenzoyl)amino-4-oxo-4H-benzopyran-2-yl]amidrazone, [6-(4-butoxybenzoyl)amino-4-oxo-4H-benzopyran-2-yl]amidrazone, [8-[4-(1,1-dimethylmethoxy)benzoyl]amino-4-oxo-4H-benzopyran-2-yl]amidrazone, [6-[4-(1,1-dimethylmethoxy)benzoyl]amino-4-oxo-4H-benzopyran-2-yl]amidrazone, [8-[4-(1,1,1-trimethylmethoxy)benzoyl]amino-4-oxo-4H-benzopyran-2-yl]amidrazone, [6-[4-(1,1,1-trimethylmethoxy)benzoyl]amino-4-oxo-4H-benzopyran-2-yl]amidrazone, [8-(4-octyloxybenzoyl)amino-4-oxo-4H-benzopyran-2-yl]amidrazone, [6-(4-octyloxybenzoyl)amino-4-oxo-4H-benzopyran-2-yl]amidrazone, [8-(4-pentadecyloxybenzoyl)amino-4-oxo-4H-benzopyran-2-yl]amidrazone, [6-(4pentadecyloxybenzoyl) amino-4-oxo-4H-benzopyran-2-yl]amidrazone, [8-[4-(3-phenylbutoxy)benzoyl]amino-4-oxo-4H-benzopyran-2-yl]amidrazone, [6-[4-(3-phenylbutoxy)benzoyl]amino-4-oxo-4H-benzopyran-2-yl]amidrazone, [8-[4-(4-phenylbutoxy)benzoyl]amino-4-oxo-4H-benzopyran-2-yl]amidrazone, [6-[4-(4-phenylbutoxy)benzoyl]amino-4-oxo-4H-benzopyran-2-yl]amidrazone, [8-[4-(8-phenyloctyloxy)benzoyl]amino-4-oxo-4H-benzopyran-2-yl]amidrazone, [6-[4-(8-phenyloctyloxy)benzoyl]amino4-oxo-4H-benzopyran-2-yl]amidrazone, (8-nitro-4-oxo-4H-benzopyran-2-yl)amidrazone, (6-nitro-4-oxo-4H-benzopyran-2-yl)amidrazone, (8-nitro-6-chloro-4-oxo-4H-benzopyran-2-yl)amidrazone and (8-nitro-6-bromo-4-oxo-4H-benzopyran-2-yl)amidrazone; and aryl group-containing amidrazones such as benzonitrile, 2-chlorobenzamidrazone, 3-chlorobenzamidrazone, 4-chlorobenzamidrazone, 2-bromobenzamidrazone, 3-bromobenzamidrazone, 4-bromobenzamidrazone, 2-fluorobenzamidrazone, 3-fluorobenzamidrazone, 4-fluorobenzamidrazone, 2-methylbenzamidrazone, 3-methylbenzamidrazone, 4-methylbenzamidrazone, 2-ethylbenzamidrazone, 3-ethylbenzamidrazone, 4-ethylbenzamidrazone, 2-propylbenzamidrazone, 3-propylbenzamidrazone, 4-propylbenzamidrazone, 2-butylbenzamidrazone, 3-butylbenzamidrazone, 4-butylbenzamidrazone, 2-octylbenzamidrazone, 3-octylbenzamidrazone, 4-octylbenzamidrazone, 2-pentadecylbenzamidrazone, 3-pentadecylbenzamidrazone, 4-pentadecylbenzamidrazone, 2-benzylbenzamidrazone, 3-benzylbenzamidrazone, 4-benzylbenzamidrazone, 2-phenethylbenzamidrazone, 3-phenethylbenzamidrazone, 4-phenethylbenzamidrazone, 2-(4-phenylbutye)benzaneidrazone, 3-(4-phenylbutyl)benzamidrazone, 4-(4-phenylbutyl)benzamidrazone, 2-(8-phenyloctyl)benzamidrazone, 3-(8-phenyloctyl)benzamidrazone, 4-(8-phenyloctyl)bbnzamidrazone, 2-(15-phenylpentadecyl)benzamidrazone, 3-(15-phenylpentadecyl)benzamidrazone, 4-(15-phenylpentadecyl)benzamidrazone, 2-methoxybenzamidrazone, 3-methoxybenzamidrazone, 4-methoxybenzamidrazone, 2-ethoxybenzamidrazone, 3-ethoxybenzamidrazone, 4-ethoxybenzamidrazone, 2-propoxybenzamidrazone, 3-propoxybenzamidrazone, 4-propoxybenzamidrazone, 2-butoxybenzamidrazone, 3-butoxybenzamidrazone, 4-butoxybenzamidrazone, 2-octyloxybenzamidrazone, 3-octyloxybenzamidrazone, 4-octyloxybenzamidrazone, 2-pentadecyloxybenzamidrazone, 3-pentadecyloxybenzamidrazone, 4-pentadecyloxybenzamidrazone, 2-benzyloxybenzamidrazone, 3-benzyloxybenzamidrazone, 4benzyloxybenzamidrazone, 2-phenethyloxybenzamidrazone, 3-phenethyloxybenzamidrazone, 4-phenethyloxybenzamidrazone, 2-(4-phenylbutoxy)benzamidrazone, 3-(4-phenylbutoxy)benzamidrazone, 4-(4-phenylbutoxy)benzamidrazone, 2-(8-phenyloctyloxy)benzamidrazone, 3-(8-phenyloctyloxy)benzamidrazone, 4-(8-phenyloctyloxy)benzamidrazone, 2-(15-phenylpentadecyloxy)benzamidrazone, 3-(15-phenylpentadecyloxy)benzamidrazone, 4-(15-phenylpentadecyloxy)benzamidrazone, 2-(1-phenyl)ethoxybenzamidrazone, 3-(1-phenyl)ethoxybenzamidrazone, 4-(1-phenyl)ethoxybenzamidrazone, (1,1'-biphen-2-yl)amidrazone, (4'-methyl-1,1'-biphen-2-yl)amidrazone, (4'-ethyl-1,1'-biphen-2-yl)amidrazone, (4'-propyl-1,1'-biphen-2-yl)amidrazone, (4'-butyl-1,1'-biphen-2-yl)amidrazone, (4'-octyl-1,1'-biphen-2-yl)amidrazone, (4'-decyl-1,1'-biphen-2-yl)amidrazone, (4'-hydroxymethyl-1,1'-biphen-2-yl)amidrazone, [4'-(2-hydroxy)ethyl-1,1'-biphen-2-yl]amidrazone, [4'-(3-hydroxy)propyl-1,1'-biphen-2-yl]amidrazone, [4'-(4-hydroxy)butyl-1,1'-biphen-2-yl]amidrazone, [4'-(8-hydroxy)octyl-1,1-biphen-2-yl]amidrazone, (4'-methoxymethyl-1,1'-biphen-2-yl)amidrazone, [4'-(2-methoxy)ethyl-1,1'-biphen-2-yl]amidrazone, [4'-(3-methoxy)propyl-1,1'-biphen-2-yl]amidrazone, [4'-(4-methoxy)butyl-1,1'-biphen-2-yl]amidrazone, [4'-(8-methoxy)octyl-1,1'-biphen-2-yl]amidrazone, (4'-benzyloxymethyl-1,1'-biphen-2-yl)amidrazone, [4'-(2-benzyloxy)ethyl-1,1'-biphen-2-yl]amidrazone, [4'-(3-benzyloxy)propyl-1, 1'-biphen-2-yl]amidrazone, [4'-(4-benzyloxy)butyl-1,1'-biphen-2-yl]amidrazone, [4'-(8-benzyloxy)octyl-1,1'-biphen-2-yl]-amidrazone, [4'-[2-(4-methoxybenzyloxy)ethyl]-1,1'-biphen-2-yl]amidrazone, [4'-[3-(4-methoxybenzyloxy)propyl]-1,1'-biphen-2-yl]amidrazone, [4'-[4-(4-methoxybenzyloxy)butyl]-1,1'-biphen-2-yl]amidrazone, [4'-[8-(4-methoxybenzyloxy)octyl]-1,1'-biphen-2-yl]amidrazone, (4'-aminomethyl-1,1'-biphen-2-yl)amidrazone,

[4'-(2-amino)ethyl-1,1'-biphen-2-yl]amidrazone, [4'-(3-amino)propyl-1,1'-biphen-2-yl]amidrazone, [4'-(4-amino)butyl-1,1'-biphen-2-yl]amidrazone, [4'-(8-amino)octyl-1,1'-biphen-2-yl]amidrazone, [4'-(N-mesylamino)methyl-1,1'-biphen-2-yl]amidrazone, [4'-(2-mesylamino)ethyl-1,1'-biphen-2-yl]amidrazone, [4'-(3-mesylamino)propyl-1,1'-biphen-2-yl]amidrazone, [4'-(4-mesylamino)butyl-1,1'-biphen-2-yl]amidrazone, [4'-(8-mesylamino)octyl-1,1'-biphen-2-yl]amidrazone, [4'-(benzyloxycarbonylamino)methyl-1,1'-biphen-2-yl]amidrazone, [4'-(2-benzyloxycarbonylamino)ethyl-1,1'-biphen-2-yl]amidrazone, [4'-(3-benzyloxycarbonylamino)propyl-1,1'-biphen-2-yl]amidrazone, [4'-(4-benzyloxycarbonylamino)butyl-1,1'-biphen-2-yl]amidrazone, [4'-(8-benzyloxycarbonylamino)octyl-1,1'-biphen-2-yl]amidrazone, [4'-(tertiary-butoxycarbonylamino)methyl-1,1'-biphen-2-yl]amidrazone, [4'-(2-tertiary-butoxycarbonylamino)ethyl-1,1'-biphen-2-yl]amidrazone, [4'-(3-tertiary-butoxycarbonylamino)propyl-1,1'-biphen-2-yl]amidrazone, [4'-(4-tertiary-butoxycarbonylamino)butyl-1,1'-biphen-2-yl]amidrazone, [4'-(8-tertiary-butoxycarbonylamino)octyl-1,1'-biphen-2-yl]amidrazone, (4'-chloromethyl-1,1'-biphen-2-yl)amidrazone, (4'-bromomethyl-1,1'-biphen-2-yl)amidrazone, [4'-(2-bromo)ethyl-1,1'-biphen-2-yl]-amidrazone, [4'-(3-bromo)propyl-1,1'-biphen-2-yl]amidrazone, [4'-(4-bromo)butyl-1,1'-biphen-2-yl]amidrazone, [4'-(8-bromo)octyl-1,1'-biphen-2-yl]amidrazone, (4'-dichloromethyl-1,1'-biphen-2-yl)amidrazone, (4'-trichloromethyl-1,1'-biphen-2-yl)amidrazone, (4'-dibromomethyl-1,1'-biphen-2-yl)amidrazone, (4'-tribromomethyl-1,'-biphen-2-yl)-amidrazone, (4'-methoxy-1,1'-biphen-2-yl)amidrazone, (4'-ethoxy-1,1'-biphen-2-yl)-amidrazone, (4'-propoxy-1,1'-biphen-2-yl)amidrazone, (4'-butoxy-1,1'-biphen-2-yl)-amidrazone, (4'-chloromethoxy-1,1'-biphen-2-yl)amidrazone and [4'-(2-chloro)ethoxy-1,1'-biphen-2-yl]amidrazone.

The reaction of amidrazone (6) or a salt thereof with nitrous acid compound (3) can be effected as follows.

The reaction of amidrazone (6) or a salt thereof with nitrous acid compound makes it possible to produce tetrazole compound (1).

The amount of nitrous acid compound (3) to be used is usually from 1 to 50 moles, relative to amidrazone (6) or a salt thereof.

When an alkali metal nitrite or an alkaline earth metal nitrite is used as the nitrous acid compound (3), an inorganic or organic acid such as hydrochloric acid, acetic acid or methanesulfonic acid is usually used together, and the amount thereof is usually from 1 to 100 moles, relative to nitrous acid compound (3).

The above reaction is usually effected in a solvent. As the solvent to be used, there can be mentioned hydrocarbons such as benzene, toluene and hexane; halogenated hydrocarbons such as dichloromethane, dichloroethane and chlorobenzene; nitrated hydrocarbons such as nitrobenzene and nitromethane; ethers such as diethyl ether and tetrahydrofuran; amides such as dimethylformamide; alcohols such as methanol and ethanol; and organic acids such as acetic acid and butyric acid. These can be used alone or as a mixture of two or more kinds of solvents. The amount of solvent to be used is usually from 3 to 200 times as much as the weight of amidrazone (6) or a salt thereof The method and order for the addition of amidrazone (6) or a salt thereof, a nitrous acid compound (and an organic or inorganic acid) and a solvent are not particularly limited, and usually, nitrous acid compound (3) may be added to a mixture of amidrazone (6) or a salt thereof, an acid and a solvent.

The reaction temperature is from −78° to +150° C., preferably from −50° to +50° C.

The end point of the reaction can be monitored by an analytical method such as liquid chromatography, and tetrazole compound (1) can be obtained, for example, by an ordinary work up such as extraction or filtration, and can also be purified, if necessary, by an ordinary technique such as recrystallization.

As the tetrazole compound thus obtained, there can be mentioned, for example, 4-oxo-4H-benzopyranyl group-containing tetrazole compounds such as 5-hydroxy-2-(tetrazol-5-yl)-4-oxo4H-benzopyran, 7-hydroxy-2-(tetrazol-5-yl)-4-oxo-4H-benzopyran, 5,7-dihydroxy-2-(tetrazol-5-yl)-4-oxo-4H-benzopyran, 5-methoxy-2-(tetrazol-5-yl)-4-oxo-4H-benzopyran, 5-ethoxy-2-(tetrazol-5-yl)-4-oxo-4H-benzopyran, 5-butoxy-2-(tetrazol-5-yl)-4-oxo-4H-benzopyran, 5-pentoxy-2-(tetrazol-5-yl)-4oxo-4H-benzopyran, 6-chloro-2-(tetrazol-5-yl)-4-oxo-4H-benzopyran, 2-(tetrazol-5-yl)-4-oxo-4H-benzopyran, 8-acetylamino-2-(tetrazol-5-yl)-4-oxo-4H-benzopyran, 6-acetylamino-2-(tetrazol-5-yl)-4-oxo-4H-benzopyran, 8-propionylamino-2-(tetrazol-5-yl)-4-oxo-4H-benzopyran, 6-propionylamino-2-(tetrazol-5-yl)-4-oxo-4H-benzopyran, 8-nonanoylamino-2-(tetrazol-5-yl)-4-oxo-4H-benzopyran, 6-nonanoylamino-2-(tetrazol-5-yl)-4-oxo-4H-benzopyran, 8-hexadecanoylamino-2-(tetrazol-5-yl)-4-oxo-4H-benzopyran, 6-hexadecanoylamino-2-(tetrazol-5-yl)-4-oxo-4H-benzopyran, 8-benzoylamino-2-(tetrazol-5-yl)-4-oxo-4H-benzopyran, 6-benzoylamino-2-(tetrazol-5-yl)-4-oxo-4H-benzopyran, 8-(3-phenylpropionyl)amino-2-(tetrazol-5-yl)-4-oxo-4H-benzopyran, 6-(3-propionyl)amino-2-(tetrazol-5-yl)-4-oxo-4H-benzopyran, 8-(9-phenylnonanoyl)amino-2-(tetrazol-5-yl)-4-oxo-4H-benzopyran, 6-(9-phenylnonanoyl)amino-2-(tetrazol-5-yl)-4-oxo-4H-benzopyran, 8-(16-phenylhexadecanoyl)amino-2-(tetrazol-5-yl)-4-oxo-4H-benzopyran, 6-(16-phenylhexadecanoyl)amino-2-(tetrazol-5-yl)-4-oxo-4H-benzopyran, 8-(4-methoxybenzoyl)amino-2-(tetrazol-5-yl)-4-oxo-4H-benzopyran, 6-(4-methoxybenzoyl)amino-2-(tetrazol-5-yl)-4-oxo-4H-benzopyran, 8-(4-ethoxybenzoyl)amino-2-(tetrazol-5-yl)-4-oxo-4H-benzopyran, 6-(4-ethoxybenzoyl)amino-2-(tetrazol-5-yl)-4-oxo-4H-benzopyran, 8-(4-propoxybenzoyl)amino-2-(tetrazol-5-yl)-4-oxo-4H-benzopyran, 6-(4-propoxybenzoyl)amino-2-(tetrazol-5-yl)-4-oxo-4H-benzopyran, 8-(4-butoxybenzoyl)amino-2-(tetrazol-5-yl)-4-oxo-4H-benzopyran, 6-(4-butoxybenzoyl)amino-2-(tetrazol-5-yl)-4-oxo-4H-benzopyran, 8-[4-(1,1-dimethylmethoxy)benzoyl]amino-2-(tetrazol-5-yl)-4-oxo-4H-benzopyran, 6-[4-(1,1-dimethylmethoxy)benzoyl]amino-2-(tetrazol-5-yl)-4-oxo-4H-benzopyran, 8-[4-(1,1,1-trimethylmethoxy)benzoyl]amino-2-(tetrazol-5-yl)-4-oxo-4H-benzopyran, 6-[4-(1,1,1-trimethylmethoxy)benzoyl]amino-2-(tetrazol-5-yl)-4-oxo-4H-benzopyran, 8-(4-octyloxybenzoyl)amino-2-(tetrazol-5-yl)-4-oxo-4H-benzopyran, 6-(4-octyloxybenzoyl)amino-2-(tetrazol-5-yl)-4-oxo-4H-benzopyran, 8-(4-pentadecyloxybenzoyl)amino-2-(tetrazol-5-yl)-4-oxo-4H-benzopyran, 6-(4-pentadecyloxybenzoyl)amino-2-(tetrazol-5-yl)-4-oxo-4H-benzopyran, 8-[4-(3-phenylbutoxy)benzoyl]amino-2-(tetrazol-5-yl)-4-oxo-4H-benzopyran, 6-[4-(3-phenylbutoxy)benzoyl]amino-2-(tetrazol-5-yl)-4-oxo-4H-benzopyran, 8-[4-(4-phenylbutoxy)benzoyl]amino-2-(tetrazol-5-yl)-4-oxo-4H-benzopyran, 6-[4-(4-phenylbutoxy)benzoyl]amino-2-(tetrazol-5-yl)-4-oxo-4H-benzopyran, 8-[4-(8-phenyloctyloxy)benzoyl]amino-2-(tetrazol-5-yl)-4-oxo-4H-benzopyran, 6-[4-(8-phenyloctyloxy)benzoyl]amino-2-(tetrazol-5-yl)-4-oxo-4H- benzopyran, 8-nitro-2-(tetrazol-5-yl)-4-oxo-4H-benzopyran, 6-nitro-2-(tetrazol-5-yl)-4-oxo-4H-benzopyran, 8-nitro-6-chloro-2-(tetrazol-5-yl)-4-oxo-4H-benzopyran and 8-nitro-6-bromo-2-(tetrazol-5-yl)-4-oxo-4H-benzopyran; and aryl group-containing tetrazole compounds such as (tetrazol-5-yl)benzene, 2-chloro-(tetrazol-5-yl)benzene, 3-chloro-(tetrazol-5-yl)benzene, 4-chloro-(tetrazol-5-yl)benzene, 2-bromo-(tetrazol-5-yl)benzene, 3-bromo-(tetrazol-5-yl)benzene, 4-bromo-(tetrazol-5-yl)benzene, 2-fluoro-(tetrazol-5-yl)benzene, 3-fluoro(tetrazol-5-yl)benzene, 4-fluoro-(tetrazol-5-yl)benzene, 2-methyl-(tetrazol-5-yl)benzene, 3-methyl-(tetrazol-5-yl)benzene, 4-methyl-(tetrazol-5-yl)benzene, 2-ethyl-(tetrazol-5-yl)benzene, 3-ethyl-(tetrazol-5-yl)benzene, 4-ethyl-(tetrazol-5-yl)benzene, 2-propyl-(tetrazol-5-yl)benzene, 3-propyl-(tetrazol-5-yl)benzene, 4-propyl-(tetrazol-5-yl)benzene, 2-butyl-(tetrazol-5-yl)benzene, 3-butyl-(tetrazol-5-yl)benzene, 4-butyl-(tetrazol-5-yl)benzene, 2-octyl-(tetrazol-5-yl)benzene, 3-octyl-(tetrazol-5-yl)benzene, 4-octyl-(tetrazol-5-yl)benzene, 2-pentadecyl-(tetrazol-5-yl)benzene, 3-pentadecyl-(tetrazol-5-yl)benzene, 4-pentadecyl-(tetrazol-5-yl)benzene, 2-benzyl-(tetrazol-5-yl)benzene, 3-benzyl-(tetrazol-5-yl)benzene, 4-benzyl-(tetrazol-5-yl)benzene, 2-phenethyl-(tetrazol-5-yl)benzene, 3-phenethyl-(tetrazol-5-yl)benzene, 4-phenethyl-(tetrazol-5-yl)benzene, 2-(4-phenylbutyl)-(tetrazol-5-yl)benzene, 3-(4-phenylbutyl)-(tetrazol-5-yl)benzene, 4-(4-phenylbutyl)-(tetrazol-5-yl)benzene, 2-(8-phenyloctyl)-(tetrazol-5-yl)benzene, 3-(8-phenyoctyl)-(tetrazol-5-yl)benzene, 4-(8-phenyloctyl)-(tetrazol-5-yl)benzene, 2-(15-phenylpentadecyl)-(tetrazol-5-yl)benzene, 3-(15-phenylpentadecyl) -(tetrazol-5-yl)benzene, 4-(15-phenylpentadecyl )(tetrazol-5-yl)benzene, 2-methoxy-(tetrazol-5-yl)benzene, 3-methoxy-(tetrazol-5-yl)benzene, 4-methoxy-(tetrazol-5-yl)benzene, 2-ethoxy-(tetrazol-5-yl)benzene, 3-ethoxy(tetrazol-5-yl)benzene, 4-ethoxy-(tetrazol-5-yl)benzene, 2-propoxy-(tetrazol-5-yl)benzene, 3-propoxy-(tetrazol-5-yl)benzene, 4-propoxy-(tetrazol-5-yl)benzene, 2-butoxy(tetrazol-5-yl)benzene, 3-butoxy-(tetrazol-5-yl)benzene, 4-butoxy-(tetrazol-5-yl)benzene, 2-octyloxy-(tetrazol-5-yl)benzene, 3-octyloxy-(tetrazol-5-yl)benzene, 4-octyloxy-(tetrazol-5-yl)benzene, 2-pentadecyloxy-(tetrazol-5-yl)benzene, 3-pentadecyloxy-(tetrazol-5-yl)benzene, 4-pentadecyloxy-(tetrazol-5-yl)benzene, 2-benzyloxy-(tetrazol-5-yl)benzene, 3-benzyloxy-(tetrazol-5-yl)benzene, 4-benzyloxy-(tetrazol-5-yl)benzene, 2-phenethyloxy-(tetrazol-5-yl)benzene, 3-phenethyloxy-(tetrazol-5-yl)benzene, 4-phenethyloxy-(tetrazol-5-yl)benzene, 2-(4-phenylbutoxy)-(tetrazol-5-yl)benzene, 3-(4-phenylbutoxy)-(tetrazol-5-yl)benzene, 4-(4-phenylbutoxy)-(tetrazol-5-yl)benzene, 2-(8-phenyloctyloxy)-(tetrazol-5-yl)benzene, 3-(8-phenyloctyloxy)-(tetrazol-5-yl)benzene, 4-(8-phenyloctyloxy)(tetrazol-5-yl)benzene, 2-(15-phenylpentadecyloxy)-(tetrazol-5-yl)benzene, 3-(15-phenylpentadecyloxy)-(tetrazol-5-yl)benzene, 4-(15-phenylpentadecyloxy)-(tetrazol-5-yl)benzene, 2-(1-phenyl)ethoxy-(tetrazol-5-yl)benzene, 3-(1-phenyl)ethoxy-(tetrazol-5-yl)benzene, 4-(1-phenyl)ethoxy-(tetrazol-5-yl)benzene, 2-(tetrazol-5-yl)-1,1'-biphenyl, 2-(tetrazol-5-yl)-4'-methyl-1,1'-biphenyl, 2-(tetrazol-5-yl)-4'-ethyl-1,1'-biphenyl, 2-(tetrazol-5-yl)-4'-propyl-1,1'-biphenyl, 2-(tetrazol-5-yl)-4'-butyl-1,1'-biphenyl, 2-(tetrazol-5-yl)-4'-octyl-1,1'-biphenyl, 2-(tetrazol-5-yl)-4'-decyl-1,1'-biphenyl, 2-(tetrazol-5-yl)-4'-hydroxymethyl-1,1'-biphenyl, 2-(tetrazol-5-yl)-4'-(2-hydroxy)ethyl-1,1'-biphenyl, 2-(tetrazol-5-yl)-4'-(3-hydroxy)propyl-1,1'-biphenyl, 2-(tetrazol-5-yl)-4'-(4-hydroxy)butyl-1,1'-biphenyl, 2-(tetrazol-5-yl)-4'-(8-hydroxy)octyl-1,1'-biphenyl, 2-(tetrazol-5-yl)-4'-methoxymethyl-1,1'-biphenyl, 2-(tetrazol-5-yl)-4'-(2-methoxy)ethyl-1,1'-biphenyl, 2-(tetrazol-5-yl)-4'-(3-methoxy)propyl-1,1'-biphenyl, 2-(tetrazol-5-yl)-4'-(4-methoxy)butyl-1,1'-biphenyl, 2-(tetrazol-5-yl)-4'-(8-methoxy)octyl-1,1'-biphenyl, 2-(tetrazol-5-yl)-4'-benzyloxymethyl-1,1'-biphenyl, 2-(tetrazol-5-yl)-4'-(2-benzyloxy)ethyl-1,1'-biphenyl, 2-(tetrazol-5-yl)-4'-(3-benzyloxy)propyl-1,1'-biphenyl, 2-(tetrazol-5-yl)4'-(4-benzyloxy)butyl-1,1'-biphenyl, 2-(tetrazol-5-yl)-4'-(8-benzyloxy)octyl-1,1'-biphenyl, 2-(tetrazol-5-yl)-4'-[2-(4-methoxybenzyloxy)ethyl]-1,1'-biphenyl, 2-(tetrazol-5-yl)-4'-[3-(4-methoxybenzyloxy)propyl]-1,1'-biphenyl, 2-(tetrazol-5-yl)-4'-[4-(4-methoxybenzyloxy)butyl]-1,1'-biphenyl, 2-(tetrazol-5-yl)-4'-[S-(4-methoxybenzyloxy)octyl]-1,1'-biphenyl, 2-(tetrazol-5-yl)-4'-aminomethyl-1,1'-biphenyl, 2-(tetrazol-5-yl)-4'-(2-amino)ethyl-1,1'-biphenyl, 2-(tetrazol-5-yl)-4'-(3-amino)propyl-1,1'-biphenyl, 2-(tetrazol-5-yl)-4'-(4-amino)butyl-1,1'-biphenyl, 2-(tetrazol-5-yl)-4'-(8-amino)octyl-1,1'-biphenyl, 2-(tetrazol-5-yl)-4'-(N-mesylamino)methyl-1,1'-biphenyl, 2-(tetrazol-5-yl)-4'-(2-mesylamino)ethyl-1,1'-biphenyl, 2-(tetrazol-5-yl)-4'-(3-mesylamino)propyl-1,1'-biphenyl, 2-(tetrazol-5-yl)-4'-(4-mesylamino)butyl-1,1'-biphenyl, 2-(tetrazol-5-yl)-4'-(8-mesylamino)octyl-1,1'-biphenyl, 2-(tetrazol-5-yl)-4'-(benzyloxycarbonylamino)methyl-1,1'-biphenyl, 2-(tetrazol-5-yl)-4'-(2-benzyloxycarbonylamino)ethyl-1,1'-biphenyl, 2-(tetrazol-5-yl)4'-(3-benzyloxycarbonylamino)propyl-1,1'-biphenyl, 2-(tetrazol-5-yl)-4'-(4-benzyloxycarbonylamino)butyl-1,1'-biphenyl, 2-(tetrazol-5-yl)-4'-(8-benzyloxycarbonylamino)octyl-1,1'-biphenyl, 2-(tetrazol-5-yl)-4'-(tertiary-butoxycarbonylamino)methyl-1,1'-biphenyl, 2-(tetrazol-5-yl)-4'-(2-tertiary-butoxycarbonylamino)ethyl-1,1'-biphenyl, 2-(tetrazol-5-yl)-4'-(3-tertiary-butoxycarbonylamino)propyl-1,1'-biphenyl, 2-(tetrazol-5-yl)-4'-(4-tertiary-butoxycarbonylamino)butyl-1,1'-biphenyl, 2-(tetrazol-5-yl)-4'-(8-tertiary-butoxycarbonylamino)octyl-1,1'-biphenyl, 2-(tetrazol-5-yl)-4'-chloromethyl-1,1'-biphenyl, 2-(tetrazol-5-yl)-4'-bromomethyl-1,1'-biphenyl, 2-(tetrazol-5-yl)-4'-(2-bromo)ethyl-1,1'-biphenyl, 2-(tetrazol-5-yl)-4'-(3-bromo)propyl-1,1'-biphenyl, 2-(tetrazol-5-yl)-4'-(4-bromo)butyl-1,1'-biphenyl, 2-(tetrazol-5-yl)-4'-(8-bromo)octyl-1,1'-biphenyl, 2-(tetrazol-5-yl)-4'-dichloromethyl-1,1'-biphenyl, 2-(tetrazol-5-yl)-4'-trichloromethyl-1,1'-biphenyl, 2-(tetrazol-5-yl)-4'-dibromomethyl-1,1'-biphenyl, 2-(tetrazol-5-yl)-4'-tribromomethyl-1,1'-biphenyl, 2-(tetrazol-5-yl)-4'-methoxy-1,1'-biphenyl, 2-(tetrazol-5-yl)-4'-ethoxy-1,1'-biphenyl, 2-(tetrazol-5-yl)-4'-propoxy-1,1'-biphenyl, 2-(tetrazol-5-yl)-4'-butoxy-1,1'-biphenyl, 2-(tetrazol-5-yl)-4'-chloromethoxy-1,1'-biphenyl and 2-(tetrazol-5-yl)-4'-(2-chloro)ethoxy-1,1'-biphenyl.

The tetrazole compound (1) can also be produced by reacting nitrile (2) with hydrogen sulfide, followed by reaction with alkyl halide (4), with hydrazine or a salt thereof, and then with nitrous acid compound (3).

The reaction of nitrile (2) with hydrogen sulfide can be effected as follows.

The reaction of nitrile (2) with hydrogen sulfide makes it possible to obtain a thioamide of general formula (7):

$$R^1C(=S)NH_2 \qquad (7)$$

wherein $R^1$ is as defined above, which corresponds to amide (5) where $R^5$ is a sulfur atom and $R^6$ is an $NH_2$ group as the production intermediate of the present invention.

The amount of hydrogen sulfide to be used is usually from 1 to 100 moles, preferably from 1 to 50 moles, and more preferably 1 to 10 moles, relative to nitrile (2). The above reaction may be effected with the addition of a base as a catalyst, typical examples of which are alkylamines such as triethylamine, tributylamine and dimethylamine. The amount thereof is usually from 1 to 20 moles, relative to nitrile (2).

The above reaction is usually effected in the presence of an organic solvent. As the solvent to be used, there can be mentioned hydrocarbons such as benzene, toluene and hexane; halogenated hydrocarbons such as dichloromethane, dichloroethane and chlorobenzene; nitrated hydrocarbons such as nitrobenzene and nitromethane; ethers such as diethyl ether and tetrahydrofuran; amides such as dimethylformamide; and alcohols such as methanol and ethanol. These can be used alone or as a mixture of two or more kinds of solvents. The amount of solvent to be used, although it can be appropriately determined, is usually from 1 to 100 times as much as the weight of nitrile (2).

The method and order for the addition of nitrile (2), hydrogen sulfide (and a base) and a solvent are not particularly limited, and usually, hydrogen sulfide may be added to a mixture of nitrile (2), a base and a solvent.

The reaction temperature is usually from −78° to +150° C., preferably from −50° to +100° C. The completion of the reaction can be monitored by an analytical method such as liquid chromatography. Usually, the disappearance of the nitrile can be considered as the end point of the reaction.

After completion of the reaction, thioamide (7) can be isolated, for example, by an ordinary procedure such as extraction or filtration, or can also be used in the next step without isolation.

As the thioamide (7) thus obtained, there can be mentioned, for example, 4-oxo-4H-benzopyranyl group-containing thioamides such as 5-hydroxy-2-thiocarbamoyl-4-oxo-4H-benzopyran, 7-hydroxy-2-thiocarbamoyl-4-oxo-4H-benzopyran, 5,7-dihydroxy-2-thiocarbamoyl-4-oxo-4H-benzopyran, 5-methoxy-2-thiocarbamoyl-4-oxo4H-benzopyran, 5-ethoxy-2-thiocarbamoyl-4-oxo-4H-benzopyran, 5-butoxy-2-thiocarbamoyl-4-oxo-4H-benzopyran, 5-pentoxy-2-thiocarbamoyl-4-oxo-4H-benzopyran, 6-chloro-2-thiocarbamoyl-4-oxo-4H-benzopyran, 2-thiocarbamoyl-4-oxo-4H-benzopyran, 8-acetylamino-2-thiocarbamoyl-4-oxo-4H-benzopyran, 6-acetylamino-2-thiocarbamoyl-4-oxo-4H-benzopyran, 8-propionylamino-2-thiocarbamoyl-4-oxo-4H-benzopyran, 6-propionylamino-2-thiocarbamoyl-4-oxo-4H-benzopyran, 8-nonanoylamino-2-thiocarbamoyl-4-oxo-4H-benzopyran, 6-nonanoylamino-2-thiocarbamoyl-4-oxo-4H-benzopyran, 8-hexadecanoylamino-2-thiocarbamoyl-4-oxo-4H-benzopyran, 6-hexadecanoylamino-2-thiocarbamoyl-4-oxo-4H-benzopyran, 8-benzoylamino-2-thiocarbamoyl-4-oxo-4H-benzopyran, 6-benzoylamino-2-thiocarbamoyl-4-oxo-4H-benzopyran, 8-(3-phenylpropionyl)amino-2-thiocarbamoyl-4-oxo-4H-benzopyran, 6-(3-propionyl)amino-2-thiocarbamoyl-4-oxo-4H-benzopyran, 8-(9-phenylnonanoyl)amino-2-thiocarbamoyl-4-oxo-4H-benzopyran, 6-(9-phenylnonanoyl)amino-2-thiocarbamoyl-4-oxo-4H-benzopyran, 8-(16-phenylhexadecanoyl)amino-2-thiocarbamoyl-4-oxo-4H-benzopyran, 6-(16-phenylhexadecanoyl)amino-2-thiocarbamoyl-4-oxo-4H-benzopyran, 8-(4-methoxybenzoyl)amino-2-thiocarbamoyl-4-oxo-4H-benzopyran, 6-(4-methoxybenzoyl)amino-2-thiocarbamoyl-4-oxo-4H-benzopyran, 8-(4-ethoxybenzoyl)amino-2-thiocarbamoyl-4-oxo-4H-benzopyran, 6-(4-ethoxybenzoyl)amino-2-thiocarbamoyl-4-oxo-4H-benzopyran, 8-(4-propoxybenzoyl)amino-2-thiocarbamoyl-4-oxo-4H-benzopyran, 6-(4-propoxybenzoyl)amino-2-thiocarbamoyl4-oxo-4H-benzopyran, 8-(4-butoxybenzoyl)amino-2-thiocarbamoyl-4-oxo-4H-benzopyran, 6-(4-butoxybenzoyl)amino-2-thiocarbamoyl-4-oxo-4H-benzopyran, 8-[4-(1,1-dimethylmethoxy)benzoyl]amino-2-thiocarbamoyl-4-oxo-4H-benzopyran, 6-[4-(1,1-dimethylmethoxy)benzoyl]amino-2-thiocarbamoyl-4-oxo-4H-benzopyran, 8-[4-(1,1,1-trimethylmethoxy)benzoyl]amino-2-thiocarbamoyl-4-oxo-4H-benzopyran, 6-[4-(,1,1-trimethylmethoxy)benzoyl]amino-2-thiocarbamoyl-4-oxo-4H-benzopyran, 8-(4-octyloxybenzoyl)amino-2-thiocarbamoyl-4-oxo-4H-benzopyran, 6-(4-octyloxybenzoyl)amino-2-thiocarbamoyl-4-oxo-4H-benzopyran, 8-(4-pentadecyloxybenzoyl)amino-2-thiocarbamoyl-4-oxo-4H-benzopyran, 6-(4-pentadecyloxybenzoyl)amino-2-thiocarbamoyl-4-oxo-4H-benzopyran, 8-[4-(3-phenylbutoxy)benzoyl]amino-2-thiocarbamoyl-4-oxo-4H-benzopyran, 6-[4-(3-phenylbutoxy)benzoyl]amino-2-thiocarbamoyl-4-oxo-4H-benzopyran, 8-[4-(4-phenylbutoxy)benzoyl]amino-2-thiocarbamoyl-4-oxo-4H-benzopyran, 6-[4-(4-phenylbutoxy) benzoyl]amino-2-thiocarbamoyl-4-oxo-4H-benzopyran, 8-[4-(8-phenyloctyloxy)benzoyl]amino-2-thiocarbamoyl-4-oxo-4H-benzopyran, 6-[4-(8-phenyloctyloxy)benzoyl]amino-2-thiocarbamoyl-4-oxo-4H-benzopyran, 8-nitro-2-thiocarbanoyl-4-oxo-4H-benzopyran, 6-nitro-2-thiocarbamoyl-4-oxo-4H-benzopyran, 8-nitro-6-nitro-2-thiocarbamoyl-4-oxo-4H-benzopyran and 8-nitro-6-bromo-2-thiocarbamoyl-4-oxo-4H-benzopyran; and aryl group-containing thioamides such as thiobenzamide, 2-chlorothiobenzamide, 3-chlorothiobenzamide, 4-chlorothiobenzamide, 2-bromothiobenzamide, 3-bromothiobenzamide, 4-bromothiobenzamide, 2-fluorothiobenzamide, 3-fluorothiobenzamide, 4-fluorothiobenzamide, 2-methylthiobenzamide, 3-methylthiobenzamide, 4-methylthiobenzamide, 2-ethylthiobenzamide, 3-ethylthiobenzamide, 4-ethylthiobenzamide, 2-propylthiobenzamide, 3-propylthiobenzamide, 4-propylthiobenzamide, 2-butylthiobenzamide, 3-butylthiobenzamide, 4-butylthiobenzamide, 2-octylthiobenzamide, 3-octylthiobenzamide, 4-octylthiobenzamide, 2-pentadecylthiobenzamide, 3-pentadecylthiobenzamide, 4-pentadecylthiobenzamide, 2-benzylthiobenzamide, 3-benzylthiobenzamide, 4-benzylthiobenzamide, 2-phenethylthiobenzamide, 3-phenethylthiobenzamide, 4-phenethylthiobenzamide, 2-(4-phenylbutyl)thiobenzamide, 3-(4-phenylbutyl)thiobenzamide, 4-(4-phenylbutyl)thiobenzamide, 2-(8-phenyloctyl)thiobenzamide, 3-(8-phenyloctyl)thiobenzamide, 4-(8-phenyloctyl)thiobenzamide, 2-(15-phenylpentadecyl)thiobenzamide, 3-(15-phenylpentadecyl)thiobenzamide, 4-(15-phenylpentadecyl)thiobenzamide, 2-ethoxythiobenzamide, 3-methoxythobenzamide, 4-methoxythiobenzamide, 2-ethoxythiobenzamide, 3-ethoxythiobenzamide, 4-ethoxythiobenzamide, 2-propoxythiobenzamide, 3-propoxythiobenzamide, 4-propoxythiobenzamide, 2-butoxythiobenzamide, 3-butoxythiobenzamide, 4-butoxythiobenzamide, 2-octyloxythiobenzamide, 3-octyloxythiobenzamide, 4-octyloxythiobenzamide, 2-pentadecyloxythiobenzamide, 3-pentadecyloxythiobenzamide, 4-pentadecyloxythiobenzamide, 2-benzyloxythiobenzamide, 3-benzyloxythiobenzamide, 4-benzyloxythiobenzamide, 2-phenethyloxythiobenzamide, 3-phenethyloxythiobenzamide, 4-phenethyloxythiobenzamide, 2-(4-phenylbutoxy)thiobenzamide, 3-(4-phenylbutoxy)thiobenzamide, 4-(4- phenylbutoxy)thiobenzamide, 2-(8-phenyloctyloxy) thiobenzamide, 3-(8-phenyloctyloxy)thiobenzamide, 4-(8-phenyloctyloxy)thiobenzamide, 2-(15-phenylpentadecyloxy)thiobenzamide, 3-(15-phenylpentadecyloxy)thiobenzamide, 4-(15-phenylpentadecyloxy)thiobenzamide, 2-(1-phenyl) ethoxythiobenzamide, 3-(1-phenyl)ethoxythiobenzamide, 4-(1-phenyl)ethoxythiobenzamide, 2-thiocarbamoyl-1,1'-biphenyl, 2-thiocarbamoyl-4'-methyl-1,1'-biphenyl, 2-thiocarbamoyl-4'-ethyl-1,1'-biphenyl, 2-thiocarbamoyl-4'-propyl-1,1'-biphenyl, 2-thiocarbamoyl-4'-butyl-1,1'-biphenyl, 2-thiocarbamoyl-4'-octyl-1,1'-biphenyl, 2-thiocarbamoyl-4'-decyl-1,1'-biphenyl, 2-thiocarbamoyl-4'-hydroxymethyl-1,1'-biphenyl, 2-thiocarbamoyl-4'-(2-hydroxy)ethyl-1,1'-biphenyl, 2-thiocarbamoyl-4'-(3-hydroxy)propyl-1,1'-biphenyl, 2-thiocarbamoyl-4'-(4-hydroxy)butyl-1,1'-biphenyl, 2-thiocarbamoyl-4'-(8-hydroxy)octyl-1,1'-biphenyl, 2-thiocarbamoyl-4'-methoxymethyl-1,1'-biphenyl, 2-thiocarbamoyl-4'-(2-methoxy)ethyl-1,1'-biphenyl, 2-thiocarbamoyl-4'-(3-methoxy)propyl-1,1'-biphenyl, 2-thiocarbamoyl-4'-(4-methoxy)butyl-1,1'-biphenyl, 2-thiocarbamoyl-4'-(8-methoxy)octyl-1,1'-biphenyl, 2-thiocarbamoyl-4'-benzyloxymethyl-1,1'-biphenyl, 2-thiocarbamoyl-4'-(2-benzyloxy)ethyl-1,1'-biphenyl, 2-thiocarbamoyl-4'-(3-benzyloxy)propyl-1,1'-biphenyl, 2-thiocarbamoyl-4'-(4-benzyloxy)butyl-1,1'-biphenyl, 2-thiocarbamoyl-4'-(8-benzyloxy)octyl-1,1'-biphenyl, 2-thiocarbamoyl-4'-[2-(4-methoxybenzyloxy)ethyl]-1,1'-biphenyl, 2-thiocarbamoyl-4'-[3-(4-methoxybenzyloxy)propyl]-1,1'-biphenyl, 2-thiocarbamoyl-4'-[4(4-methoxybenzyloxy)butyl]-1,1'-biphenyl, 2-thiocarbamoyl-4'-[8-(4-methoxybenzyloxy)octyl]-1,1'-biphenyl, 2-thiocarbamoyl-4'-aminomethyl-1,1'-biphenyl, 2-thiocarbamoyl-4'-(2-amino)ethyl-1,1'-biphenyl, 2-thiocarbamoyl-4'-(3-amino)propyl-1,1'-biphenyl, 2-thiocarbamoyl-4'-(4-amino)butyl-1,1'-biphenyl, 2-thiocarbamoyl-4'-(8-amino)octyl-1,1'-biphenyl, 2-thiocarbamoyl-4'-(N-mesylamino)methyl-1,1'-biphenyl, 2-thiocarbamoyl-4'-(2-mesylamino)ethyl-1,1'-biphenyl, 2-thiocarbamoyl-4'-(3-mesylamino)propyl-1,1'-biphenyl, 2-thiocarbamoyl-4'-(4-mesylamino)butyl-1,1'-biphenyl, 2-thiocarbamoyl-4'-(8-mesylamino)octyl-1,1'-biphenyl, 2-thiocarbamoyl-4'-(benzyloxycarbonylamino)methyl-1,1'-biphenyl, 2-thiocarbamoyl-4'-(2-benzyloxycarbonylamino)ethyl-1,1'-biphenyl, 2-thiocarbamoyl-4'-(3-benzyloxycarbonylamino)propyl-1,1'-biphenyl, 2-thiocarbamoyl-4'-(4-benzyloxycarbonylamino)butyl-1,1'-biphenyl, 2-thiocarbamoyl-4'-(8-benzyloxycarbonylamino) octyl-1,1'-biphenyl, 2-thiocarbamoyl-4'-(tertiary-butoxycarbonylamino)methyl-1,1'-biphenyl, 2-thiocarbamoyl-4'-(2-tertiarybutoxycarbonylamino)ethyl-1,1'-biphenyl, 2-thiocarbamoyl-4'-(3-tertiary-butoxycarbonylamino)propyl-1,1'-biphenyl, 2-thiocarbamoyl-4'-(4-tertiary-butoxycarbonylamino)-butyl-1,1'-biphenyl, 2-thiocarbamoyl-4'-(8-tertiary-butoxycarbonylamino)octyl-1,1'-biphenyl, 2-thiocarbamoyl-4'-chloromethyl-1,1'-biphenyl, 2-thiocarbamoyl-4'-bromomethyl-1,1'-biphenyl, 2-thiocarbamoyl-4'-(2-bromo)ethyl-1,1'-biphenyl, 2-thiocarbamoyl-4'-(3-bromo)propyl-1,1'-biphenyl, 2-thiocarbamoyl-4'-(4-bromo)butyl-1,1'-biphenyl, 2-thiocarbamoyl-4'-(8-bromo)octyl-1,1'-biphenyl, 2-thiocarbamoyl-4'-dichloromethyl-1,1'-biphenyl, 2-thiocarbamoyl-4'-trichloromethyl-1,1'-biphenyl, 2-thiocarbamoyl-4'-dibromomethyl-1,1'-biphenyl, 2-thiocarbamoyl-4'-tribromomethyl-1,1'-biphenyl, 2-thiocarbamoyl-4'-methoxy-1,1'-biphenyl, 2-thiocarbamoyl-4'-ethoxy-1,1'-biphenyl, 2-thiocarbamoyl-4'-propoxy-1,1'-biphenyl, 2-thiocarbamoyl-4'-butoxy-1,1'-biphenyl, 2-thiocarbamoyl-4'-chloromethoxy-1,1'-biphenyl and 2-thiocarbamoyl-4'-(2-chloro)ethoxy-1,1'-biphenyl.

The reaction of thioamide (7) with alkyl halide (4) can be effected as follows.

The reaction of thioamide (7) with alkyl halide (4) makes it possible to obtain a hydrogen halide salt of an isothioamide of general formula 8:

$$R^1(=NH)SR^4 \tag{8}$$

wherein $R^1$ and $R^4$ are as defined above, which corresponds to amide (5) where $R^5$ is an NH group and $R^6$ is an $SR^4$ group as the production intermediate of the present invention.

As the alkyl halide (4) to be used, there can be mentioned, for example, $C_1$–$C_{20}$, preferably $C_1$–$C_{10}$, and more preferably $C_1$–$C_5$, alkyl halides such as methyl iodide, ethyl iodide, butyl iodide, butyl bromide, pentyl bromide and pentyl iodide. The amount thereof may be usually 1 mole or more, preferably from about 1 to about 5 moles, relative to thioamide (7).

The above reaction is usually effected in an organic solvent. As such a solvent, there can be mentioned, for example, hydrocarbons such as benzene, toluene and hexane; halogenated hydrocarbons such as dichloromethane, dichloroethane and chlorobenzene; nitrated hydrocarbons such as nitrobenzene and nitromethane; ethers such as diethyl ether and tetrahydrofuran; amides such as dimethylformamide; alcohols such as methanol and ethanol; and ketones such as acetone, methyl ethyl ketone and methyl isobutyl ketone. These can be used alone or as a mixture of two or more kinds of solvents. The amount of solvent to be used can be appropriately determined.

The method and order for the addition of thioamide (7), alkyl halide (4) and a solvent are not particularly limited, and usually, alkyl halide (4) may be added to a mixture of thioamide (7) and a solvent.

The reaction temperature is usually from −78° to +150° C., preferably from −50° to +100° C. The completion of the reaction can be monitored by an analytical method such as liquid chromatography. Usually, the disappearance of thioamide (7) can be considered as the end point of the reaction.

After completion of the reaction, a hydrogen halide salt of isothioamide (8) can be isolated, for example, by an ordinary procedure such as extraction or filtration, or can also be used in the next step without isolation.

As the hydrogen halide salt of isothioamide (8) thus obtained, there can be mentioned, for example, 4-oxo-4H-benzopyranyl group-containing isothioamides such as 5-hydroxy-2-(S-methyl)isothiocarbamoyl-4-oxo-4H-benzopyran, 7-hydroxy-2-(S-methyl)isothiocarbamoyl-4-oxo-4H-benzopyran, 5,7-dihydroxy-2-(S-methyl) isothiocarbamoyl-4-oxo-4H-benzopyran, 5-methoxy-2-(S-methyl)isothiocarbamoyl-4-oxo4H-benzopyran, 5-ethoxy-2-(S-methyl)isothiocarbamoyl-4-oxo-4H-benzopyran, 5-butoxy-2-(S-methyl)isothiocarbamoyl-4-oxo-4H-benzopyran, 5-pentoxy-2-(S-methyl)isothiocarbamoyl-4-oxo-4H-benzopyran, 6-chloro-2-(S-methyl) isothiocarbamoyl-4-oxo-4H-benzopyran, 2-(S-methyl) isothiocarbamoyl-4-oxo-4H-benzopyran, 8-acetylamino-2-(S-methyl)isothiocarbamoyl-4-oxo-4H-benzopyran, 6-acetylamino-2-(S-methyl)isothiocarbamoyl-4-oxo-4H-benzopyran, 8-propionylamino-2-(S-methyl) isothiocarbamoyl-4-oxo-4H-benzopyran, 6-propionylamino-2-(S-methyl)isothiocarbamoyl-4-oxo-4H-benzopyran, 8-nonanoylamino-2-(S-methyl)

isothiocarbamoyl-4-oxo-4H-benzopyran, 6-nonanoylamino-2-(S-methyl)isothiocarbamoyl-4-oxo-4H-benzopyran, 8-hexadecanoylamino-2-(S-methyl)isothiocarbamoyl-4-oxo-4H-benzopyran, 6-hexadecanoylamino-2-(S-methyl)-isothiocarbamoyl-4-oxo-4H-benzopyran, 8-benzoylamino-2-(S-methyl)isothiocarbamoyl-4-oxo-4H-benzopyran, 6-benzoylamino-2-(S-methyl)isothiocarbamoyl-4-oxo-4H-benzopyran, 8-(3-phenylpropionyl)amino-2-(S-methyl)isothiocarbamoyl-4-oxo-4H-benzopyran, 6-(3-propionyl)amino-2-(S-methyl)isothiocarbamoyl-4-oxo-4H-benzopyran, 8-(9-phenylnonanoyl)amino-2-(S-methyl)isothiocarbamoyl-4-oxo-4H-benzopyran, 6-(9-phenylnonanoyl)amino-2-(S-methyllisothiocarbamoyl-4-oxo-4H-benzopyran, 8-(16-phenylhexadecanoyl)amino-2-(S-methyl)isothiocarbamoyl-4-oxo-4H-benzopyran, 6-(16-phenylhexadecanoyl)amino-2-(S-methyl)isothiocarbamoyl-4-oxo-4H-benzopyran, 8-(4-methoxybenzoyl)amino-2-(S-methyl)isothiocarbamoyl-4-oxo-4H-benzopyran, 6-(4-methoxybenzoyl)amino-2-(S-methyl)isothiocarbamoyl-4-oxo-4H-benzopyran, 8-(4-ethoxybenzoyl)amino-2-(S-methyl)isothiocarbamoyl-4-oxo-4H-benzopyran, 6-(4-ethoxybenzoyl)amino-2-(S-methyl)isothiocarbamoyl-4-oxo-4H-benzopyran, 8-(4-propoxybenzoyl)amino-2-(S-methyl)isothiocarbamoyl-4-oxo-4H-benzopyran, 6-(4-propoxybenzoyl)amino-2-(S-methyl)isothiocarbamoyl-4-oxo4H-benzopyran, 8-(4-butoxybenzoyl)amino-2-(S-methyl)isothiocarbamoyl-4-oxo-4H-benzopyran, 6-(4-butoxybenzoyl)amino-2-(S-methyl)isothiocarbamoyl-4-oxo-4H-benzopyran, 8-[4-(1,1-dimethylmethoxy)benzoyl]-amino-2-(S-methyl)isothiocarbamoyl-4-oxo-4H-benzopyran, 6-[4-(1,1-dimethylmethoxyl)benzoyl]amino-2-(S-methyl)isothiocarbamoyl-4-oxo-4H-benzopyran, 8-[4-(1,1,1-trimethylmethoxy)benzoyl]amino-2-(S-methyl)isothiocarbamoyl-4-oxo-4H-benzopyran, 6-[4-(1,1,1-trimethylmethoxy)benzoyl]amino-2-(S-methyl)isothiocarbamoyl-4-oxo-4H-benzopyran, 8-(4-octyloxybenzoyl)amino-2-(S-methyl)isothiocarbamoyl-4-oxo-4H-benzopyran, 6-(4-octyloxybenzoyl)amino-2-(S-methyl)isothiocarbamoyl-4-oxo-4H-benzopyran, 6-(4-pentadecyloxybenzoyl)amino-2-(S-methyl)isothiocarbamoyl-4-oxo-4H-benzopyran, 8-(4-octyloxybenzoyl)amino-2-(S-methyl)isothiocarbamoyl-4-oxo-4H-benzopyran, 6-(4-octyloxybenzoyl)amino-2-(S-methyl)isothiocarbamoyl-4-oxo-4H-benzopyran, 8-(4-pentadeecyloxybenzoyl)amino-2-(S-methyl)isothiocarbamoyl-4-oxo-4H-benzopyran, 6-(4-pentadecyloxybenzoyl)amino-2-(S-methyl)isothiocarbamoyl-4-oxo-4H-benzopyran, 8-[4-(3-phenylbutoxy)benzoyl]amino-2-(S-methyl)isothiocarbamoyl-4-oxo-4H-benzopyran, 6-[4-(3-phenylbutoxy)benzoyl]amino-2-(S-methyl)isothiocarbamoyl-4-oxo-4H-benzopyran, 8-[[4(4-phenylbutoxy )benzoyl]amino-2-(S-methyl)isothiocarbamoyl-4-oxo-4H-benzopyran, 6-[4-(4-phenylbutoxy)benzoyl]amino-2-(S-methyl)isothiocarbamoyl-4-oxo-4H -benzopyran, 8-[4-(8-phenboctytoxy)benzoyl ]amino-2-(S-methyl)isothiocarbamoyl-4-oxo-4H-benzopyran, 6-[4-(8-phenyloctyloxy)benzoyl]amino-2-(S-methyl)isothiocarbamoyl-4-oxo-4H-benzopyran, 8-nitro-2-(S-methyl)isothiocarbamoyl-4-oxo-4H-benzopyran, 6-nitro-2-(S-methyl)isothiocarbamoyl-4-oxo-4H-benzopyran, 8-nitro-6-chloro-2-(S-methyl)isothiocarbamoyl-4-oxo-4H-benzopyran and 8-nitro-6-bromo-2-(S-methyl)isothiocarbamoyl-4-oxo-4H-benzopyran; and aryl group-containing isothioamides such as (S-methyl)isothiobenzamide, 2-chloro-(S-methyl)isothiobenzamide, 3-chloro-(S-methyl)isothiobenzamide, 4-chloro-(S-methyl)isothiobenzamide, 2-bromo-(S-methyl)isothiobenzamide, 3-bromo-(S-methyl)isothiobenzamiide, 4bromo-(S-methyl)isothiobenzamide, 2-fluoro-(S-methyl)isothiobenzamide, 3-fluoro-(S-methyl)isothiobenzamide, 4-fluoro-(S-methyl)isothiobenzamide, 2-methyl-(S-methyl)isothiobenzamide, 3-methyl-(S-methyl)isothiobenzamide, 4-methyl-(S-methyl)isothiobenzamide, 2-ethyl-(S-methyl)isothiobenzamide, 3-ethyl-(S-methyl)isothiobenzamide, 4-ethyl-(S-methyl)isothiobenzamide, 2-propyl-(S-methyl)isothiobenzamide, 3-propyl-(S-methyl)isothiobenzamide, 4-propyl-(S-methyl)isothiobenzamide, 2-butyl-(S-methyl)isothiobenzamide, 3-butyl-(S-methyl)isothiobezamide, 4-butyl-(S-methyl)isothiobenzamide, 2-octyl-(S-methyl)isothiobenzamide, 3-octyl-(S-methyl)isothiobenzamide, 4-octyl-(S-methyl) isothiobenzamide, 2-pentadecyl-(S-methyl) isothobenzamide, 3-peotadecyl-(S-methyl)isothiobenzamide, 4-pentadecyl-(S-methyl)isothiobenzamide, 2-benzyl-(S-methyl)isothiobenzamide, 3-benzyl-(S-methyl)isothiobenzamide, 4-benzyl-(S-methyl)isothiobenzamide, 2-phenethyl-(S-methyl)isothiobenzamide, 3-phenethyl-(S-methyl)isothiobenzamide, 4-phenethyl-(S-methyl)isothiobenzamide, 2-(4-phenylbutyl)-(S-methyl)isothiobenzamide, 3-(4-phenylbutyl)-(S-methyl)isothiobenzamide, 4-(4-phenylbutyl)-(S-methyl)isothiobenzamide, 2-(8-phenyloctyl)-(S-methyl)isothiobenzamide, 3-(8-phenyboctyl)-(S-methyl)isothiobenzamide, 4-(8-phenyloctyl) -(S-methyl)isothiobenzamide, 2-(15-phenylpentadecyl)-(S-methyl)isothiobenzamide, 3-(15-phenylpentadecyl)-(S-methyl)isothiobenzamide, 4-(15-phenylpentadecyl)-(S-methyl)isothiobenzamide, 2-methoxy-(S-methyl)-isothiobenzamide, 3-methoxy-(S-methyl)isothiobenzamide, 4-methoxy-(S-methyl)isothiobenzamide, 2-ethoxy-(S-methyl)isothiobenzamide, 3-ethoxy-(S-methyl)isothiobenzamide, 4-ethoxy-(S-methyl)isothiobenzamide, 2-propoxy-(S-methyl)isothiobenzamide, 3-propoxy-(S-methyl)isothiobenzamide, 4-propoxy-(S-methy)isothiobenzamide, 2-butoxy-(S-methyl)isothiobenzamide, 3-butoxy-(S-methyl)isothiobenzamide, 4-butoxy-(S-methyl)isothiobenzamide, 2-octyloxy-(S-methyl)isothiobenzamide, 3-octyloxy-(S-methyl)isothiobenzaImide, 4-octyloxy-(S-methyl)isothiobenzamide, 2-pentadecyloxy-(S-methyl)isothiobenzamide, 3-pentadecyloxy-(S-methyl)isothiobenzamide, 4-pentadecyloxy-(S-methyl)isothiobenzamide, 2-benzyloxy-(S-methyl)isothiobenzamide, 3-benzyloxy-(S-methyl)isothiobenzamide, 4-benzyloxy-(S-methyl)isothiobenzamide, 2-phenethyloxy-(S-methyl)isothiobenzamide, 3-phenethyl(S-methyl)isothiobenzamide, 4-phenethyloxy-(S-methyl)isothiobenzamide, 2-(4phenylbutoxy)-(S-methyl)isothiobenzamide, 3-(4-phenylbutoxy)-(S-methyl)isothiobenzamide, 4-(4-phenylbutoxy)-(S-methyl)isothiobenzamide, 2-(8-phenyloctyloxy)-(S-methyl)isothiobenzamide, 3-(8-phenyloctyloxy)-(S-methyl)isothiobenzamide, 4-(8-phenyloctyloxy)-(S-methyl)isothiobenzamide, 2-(15-phenylpentadecyloxy)-(S-methyl)isothlobenzamide, 3-(15-phenylpentadecyloxy)-(S-methyl)isothiobenzamide, 4-(15-phenylpentadecyloxy)-(S-methyl)isothiobenzamide, 2-(l1-phenyl)ethoxy-(S-methyl)isothiobenzamide, 3-(4-phenyl)ethoxy-(S-methyl)isothiobenzamide, 4-(8-phenyl)ethoxy-(S-methyl)isothiobenzamide, 2-(S-methyl)isothiocarbamoyl-1,1'-biphenyl, 2-(S-methyl)isothiocarbamoyl-4'-methyl-1,1'-biphenyl, 2-(S-methyl)

isothiocarbamoyl-4-methyl-1,1-biphenyl, 2-(S-methyl) isothiocarbamoyl-4'-propyl-1,1'-biphenyl, 2-(S-methyl) isothiocarbamoyl-4'-butyl-1,1'-biphenyl, 2-(S-methyl) isothiocarbamoyl-4'-octyl-1,1'-biphenyl, 2-(S-methyl) isothiocarbamoyl-4'-decyl-1,1'-biphenyl, 2-(S-methyl) isothiocarbamoyl-4'-hydroxymethyl-1,1'-biphenyl, 2-(S-methyl)isothiocarbamoyl-4'-(2-hydroxy)ethyl-1,1'-biphenyl, 2-(S-methyl)isothiocarbamoyl-4'-(3-hydroxy)propyl-1,1'-biphenyl, 2-(S-methyl)isothiocarbamoyl-4'-(4-hydroxy)butyl-1,1'-biphenyl, 2-(S-methyl)isothiocarbamoyl-4'-(8-hydroxy)octyl-1,1'-biphenyl, 2-(S-methyl)isothiocarbamoyl-4'-methoxymethyl-1,1'-biphenyl, 2-(S-methyl)isothiocarbamoyl-4'-(2-methoxy)ethyl-1,1'-biphenyl, 2-(S-methyl)isothiocarbamoyl-4'-(3-methoxy)propyl-1,1'-biphenyl, 2-(S-methyl)isothiocarbamoyl-4'-(4-methoxy)butyl-1,1'-biphenyl, 2-(S-methyl)isothiocarbamoyl-4'-(8-methoxy)octyl-1,1'-biphenyl, 2-(S-methyl)isothiocarbamoyl-4'-benzyloxymethyl-1,1'-biphenyl, 2-(S-methyl)isothiocarbamoyl-4'-(2-benzyloxy)ethyl-1,1'-biphenyl, 2-(S-methyl)isothiocarbamoyl-4'-(3-benzyloxy)propyl-1,1'-biphenyl, 2-(S-methyl)isothiocarbamoyl-4'-(4-benzyloxy)butyl-1,1'-biphenyl, 2-(S-methyl)isothiocarbamoyl-4'-(8-benzyloxy)octyl-1,1'-biphenyl, 2-(S-methyl)isothiocarbamoyl-4'-2-(4-methoxybenzyloxy)ethyl]-1,1'-biphenyl, 2-(S-methyl) isothiocarbamoyl-4'-[3-(4-methoxybenzyloxy)propyl]-1,1'-biphenyl, 2-(S-methyl)isothiocarbamoyl-4'-[4-(4-methoxybenzyloxy)butyl]-1,1'-biphenyl, 2-(S-methyl) isothiocarbamoyl-4'-[8-(4-methoxybenzyloxy)octyl]-1,1'-biphenyl, 2-(S-methyl)isothiocarbamoyl-4'-aminomethyl-1,1'-biphenyl, 2-(S-methyl)isothiocarbamoyl-4'-(2-amino)ethyl-1,1'-biphenyl, 2-(S-methyl)isothiocarbamoyl-4'-(3-amino)propyl-1,1'-biphenyl, 2-(S-methyl)isothiocarbamoyl-4'-(4-amino)butyl-1,1'-biphenyl, 2-(S-methyl) isothiocarbamoyl-4'-(8-amino)octyl-1,1'-biphenyl, 2-(S-methyl)isothiocarbamoyl-4'-(N-mesylamino) methyl-1,1'-biphenyl, 2-(S-methyl)isothiocarbamoyl-4'-(2-mesylamino)ethyl-1,1'-biphenyl, 2-(S-methyl)isothiocarbamoyl-4'-(3-mesylamino)propyl-1,1'-biphenyl, 2-(S-methyl) isothiocarbamoyl-4'-(4-mesylamino)butyl-1,1'-biphenyl, 2-(S-methyl)isothiocarbamoyl-4'-(8-mesylamino)octy,1,1'-biphenyl, 2-(S-methyl)isothiocarbamoyl-4'-(benzyloxycarbonylarnno)methyl-1,1'-biphenyl, 2-(S-methyl)isothiocarbamoyl-4'-(2-benzyloxycarbonylamino)ethyl-1,1,'-biphenyl, 2-(S-methyl)isothiocarbamoyl-4'-(3-benzyloxycarbonylamino)propyl-1,1'-biphenyl, 2-(S-methyl)isothiocarbamoyl-4'-(4-benzyloxycarbonylamino)butyl-1,I'-biphenyl, 2-(S-methyl)isothiocarbamoyl-4'-(8-benzyloxycarbonylamino)octyl-1,1'-biphenyl, 2-(S-methyl) isothiocarbamoyl-4'-(tertiary-butoxycarbonylamino) methyl-1,1'-biphenyl, 2-(S-methyl)isothiocarbamoyl-4'-(2-tertiary-butoxycarbonylamino)ethyl-1,1'-biphenyl, 2-(S-methyl)isothiocarbamoyl-4'-(3-tertiary-butoxycarbonylamino)propyl-1,1'-biphenyl, 2-(S-methyl) isothiocarbamoyl-4'-(4-tertiary-butoxycarbonylamino) butyl-1,1'-biphenyl, 2-(S-methyl)isothiocarbamoyl-4'-(8-tertiary-butoxycarbonylamino)octyl-1,1'-biphenyl, 2-(S-methyl)isothiocarbamoyl-4'-chloromethyl-1,1'-biphenyl, 2-(S-methyl)isothiocarbamoyl-4'-bromomethyl-1,1'-biphenyl, 2-(S-methyl)isothiocarbamoyl-4'-(2-bromo)ethyl-1,1'-biphenyl, 2-(S-methyl)isothiocarbamoyl-4'-(3-bromo)propyl-1,1'-biphenyl, 2-(S-methyl)isothiocarbamoyl-4'-(4-bromo)butyl-1,1'-biphenyl, 2-(S-methyl)isothiocarbamoyl-4'-(8-bromo)octyl-1,1'-biphenyl, 2-(S-methyl) isothiocarbamoyl-4'-dichloromethyl-1,1'-biphenyl, 2-(S-methyl)isothiocarbamoyl-4'-trichloromethyl-1,1'-biphenyl, 2-(S-methyl)isothiocarbamoyl-4'-dibromomethyl-1,1'-biphenyl, 2-(S-methyl)isothiocarbamoyl-4'-tribromomethyl-1,1'-biphenyl, 2-(S-methyl) isothiocarbamoyl-4'-methoxy-1,1'-biphenyl, 2-(S-methyl)-isothiocarbamoyl-4'-ethoxy-1,1'-biphenyl, 2-(S-methyl) isothiocarbamoyl-4'-propoxy-1,1'-biphenyl, 2-(S-methyl) isothiocarbamoyl-4'-butoxy-1,1'-biphenyl, 2-(S-methyl) isothiocarbamoyl-4'-chloromethoxy-1,1'-biphenyl and 2-(S-methyl)isothiocarbamoyl-4'-(2-chloro)ethoxy-1,1'-biphenyl.

The reaction of a hydrogen halide salt of isothioamide (8) with hydrazine or a salt thereof can be effected as follows.

The reaction of a hydrogen halide salt of isothioamide (8) with hydrazine or a salt thereof makes it possible to obtain a hydrogen halide salt of amidrazone (6) which corresponds to amide (5) where $R^5$ is an NH group and $R^6$ is an $NHNH_2$ group as the production intermediate of the present invention.

The amount of hydrazine or a salt thereof, which is to be used, is usually from 1 to 20 moles, relative to isothioamide (8).

The above reaction is usually effected in the presence of an organic solvent. As the solvent to be used, there can be mentioned those which are inert to hydrazine or salts thereof, for example, hydrocarbons such as benzene, toluene and hexane; halogenated hydrocarbons such as dichloromethane, dichloroethane and chlorobenzene; nitrated hydrocarbons such as nitrobenzene and nitromethane; ethers such as diethyl ether and tetrahydrofuran; amides such as dimethylformamide; and alcohols such as methanol and ethanol. These can be used alone or as a mixture of two or more kinds of solvents. The amount of solvent to be used, although it can be appropriately determined, is usually from 1 to 100 times as much as the weight of isothioamide (8).

There is no particular need to use any reaction additive such as another catalyst in the above reaction. When such a reaction additive is added, a base can be used, examples of which are pyridine compounds and alkylamines, such as pyridine, 2-methyl-5-ethylpyridine, triethylamine and tributylamine. The amount thereof is usually from 0.001 to 5 moles, preferably from 0.01 to 5 moles, and more preferably 0.1 to 5 moles, relative to the hydrogen halide salt of isothioamide (8).

The method and order for the addition of isothioamide (8), hydrazine or a salt thereof and a catalyst are not particularly limited, and usually, hydrazine or a salt thereof may be added to a mixture of isothloamide (9) and a solvent (and a base).

The reaction temperature is usually from −78° to +150° C., preferably from −50° to +100° C. The completion of the reaction can be monitored by an analytical method such as liquid chromatography. Usually, the disappearance of isothioamide (8) can be considered as the end point of the reaction.

After completion of the reaction, a hydrogen halide salt of amidrazone (6) can be isolated, for example, by an ordinary procedure such as extraction or filtration.

In general, amidrazone (6) is often unstable in free form, and therefore, when isolated, amidrazone (6) is preferably converted into its salt with hydrogen halide or the like.

The amidrazone (6) or a salt thereof can also be obtained by reacting thioamide (7) with hydrazine or a salt thereof.

This reaction can be effected similarly to the above reaction of a hydrogen halide salt of isothioamide (8) with hydrazine or a salt thereof.

The reaction of a hydrogen halide salt of amidrazone (6) with nitrous acid compound (3) can be effected as follows.

The reaction of a hydrogen halide salt of amidrazone (6) with a nitrous acid compound makes it possible to produce tetrazole compound (1).

This reaction can be effected similarly to the above reaction of amidrazone (6) with nitrous acid compound (3).

Thus, according to the present invention, it is possible to produce tetrazole compounds in a simple and industrially favorable manner without using any azide or any tin compound which is not desirable from the viewpoint of safety and waste matters treatment. The amide (5), which is the compound of the present invention, is useful as an intermediate for the production of tetrazole compounds.

The present invention will be further illustrated by the following examples, but the present invention is not limited to these examples.

EXAMPLE 1

First, 2.0 g (4.56 mmol) of 8-[4-(4-phenylbutoxy) benzoyl]amino-2-cyano-4-oxo-4H-benzopyran was suspended in a mixture of 52 g of toluene, 0.23 g (2.28 mmol) of triethylamine and 15 g of methanol, and 0.155 g of hydrogen sulfide gas (hydrogen sulfide, 4.7 mmol) was bubbled thereinto at room temperature. After stirring at room temperature for 3 hours, the completion of the reaction was checked by liquid chromatography, and the reaction mixture was concentrated to give the corresponding thioamide. Product amount, 2.15 g; yield, 99%; m.p., 203–208° C.

EXAMPLES 2–5

The reaction in Example 1 was effected in the same manner as described in Example 1, except that 2-cyano-4-oxo-4H-benzopyran, 5-hydroxy-2-cyano-4-oxo-4H-benzopyran, 6-chloro-2-cyano-4-oxo-4H-benzopyran or 8-nitro-2-cyano-4-oxo-4H-benzopyran was used in place of 8-[4-(4-phenylbutoxy)benzoyl]amino-2-cyano-4-oxo-4H-benzopyran, and the corresponding thioamide was obtained.

The results are shown in Table 1.

TABLE 1

| Example | Starting Material Name |
|---|---|
| 2 | 2-Cyano-4-oxo-4H-benzopyran |
| 3 | 5-Hydroxy-2-cyano-4-oxo-4H-benzopyran |
| 4 | 6-Chloro-2-cyano-4-oxo-4H-benzopyran |
| 5 | 8-Nitro-2-cyano-4-oxo-4H-benzopyran |
| | Product |
| 2 | 2-Thiocarbamoyl-4-oxo-4H-benzopyran Yield, 88%; m.p., 225–231° C. |
| 3 | 5-Hydroxy-2-thiocarbamoyl-4-oxo-4H-benzopyran Yield, 98% |
| 4 | 6-Chloro-2-thiocarbamoyl-4-oxo-4H-benzopyran Yield, 95%; m.p., 284–289° C. |
| 5 | 6-Nitro-2-thiocarbamoyl-4-oxo-4H-benzopyran Yield, 97%; m.p., 223–228° C. |

EXAMPLE 6

First, 2.00 g of 2-cyano4'-methyl-1,1'-biphenyl was dissolved in a mixture of 15 ml of methanol and 4.18 g of triethylamine, and hydrogen sulfide gas was bubbled thereinto at room temperature to the point of saturation. After keeping at room temperature for 3 days, the solution was kept at 50° C. for 6 hours. The reaction mixture was concentrated under reduced pressure, and the residue was extracted with ethyl acetate containing 1% hydrochloric acid. The organic layer was concentrated to give 2.18 g of 2-thiocarbamoyl-4'-methyl-1,1'-biphenyl. Yield, 92%; m.p., 111–115° C.; m/z, 227

EXAMPLES 7–8

The procedures were repeated according to Example 6, except that the following nitriles were used. The results are in Table 2.

TABLE 2

| Example | Starting Material Name |
|---|---|
| 7 | 2-Chlorobenzonitrile |
| 8 | 2-Cyano-1,1'-biphenyl |
| Example | Product |
| 7 | 2-Chlorobenzthioamide Yield, 93% |
| 8 | 2-Thiocarbamoyl-1,1'-biphenyl Yield, 95% |

EXAMPLE 9

First, 2.15 g (4.55 mmol) of 8-[4-(4-phenylbutoxy) benzoyl]amino-2-thiocarbamoyl-4-oxo-4H-benzopyran was suspended in a mixture of 50 g of toluene and 10 g of methanol, and 0.15 g (4.56 mmol) of anhydrous hydrazine was added thereto at 0° C. After stirring at 0–5° C. for 8 hours, the reaction mixture was filtered to give [8-[4-(4-phenylbutoxy)benzoyl]amino-4-oxo-4H-benzopyran-2-yl] amidrazone. Product amount, 1.81 g; yield, 85%; m.p., 183–186° C.

EXAMPLE 10

First, 2.00 g (4.52 mmol) of 8-[4-(4-phenylbutoxy) benzoyl]amino-2-cyano-4-oxo-4H-benzopyran and 0.69 g (6.77 mmol) of triethylamine were dissolved in 60 ml of dichloromethane, and 0.33 g (4.74 mmol) of hydrazine hydrochloride was added thereto, followed by keeping at 40° C. for 96 hours.

The reaction mixture was filtered to give 1.72 g of [8-[4-(4-phenylbutoxy)benzoyl]amino4-oxo-4H-benzopyran-2-yl]amidrazone. Yield, 81%

EXAMPLE 11

The reaction in Example 9 was effected in the same manner as described in Example 9, except that 6-chloro-2-thiocarbamoyl-4-oxo-4H-benzopyran was used in place of 8-[4-(4-phenylbutoxy)benzoyl]amino-2-thiocarbamoyl-4-oxo-4H-benzopyran, and 2-(6-chloro-4-oxo-4H-benzopyran-2-yl)amidrazone was obtained in 85% yield.

EXAMPLE 12

The procedure in Example 9 was repeated in the same manner as described in Example 9, except that 2-chlorobenzthioamide was used in place of 8-[4-(4-phenylbutoxy)benzoyl]amino-2-thiocarbamoyl-4-oxo-4H-benzopyran and hexane was added after the reaction at 60° C. for 48 hours, and 2-chloro-benzamidrazone was-obtained in 78% yield.

EXAMPLE 13

First, 1.50 g of 2-thiocarbamoyl-4'-methyl-1,1'-biphenyl was dissolved in 20 ml of acetone, and 1.10 g of methyl iodide was added thereto. At 0° C. to room temperature, stirring was continued overnight. To the reaction mixture was added 45 ml of toluene, followed by filtration, and 1.57 g of (4'-methyl-1,1'-biphen-2-yl)-S-methylisothioamide hydroiodide was obtained. Yield, 87%; m.p., 165–169° C. (decomp.)

EXAMPLE 14

First, 1.00 g of 2-chlorobenzthioamide was dissolved in 10 ml of acetone, and 1.17 g of methyl iodide was added thereto. At 0° C. to room temperature, stirring was continued overnight. To the reaction mixture was added 40 ml of ether, followed by filtration, and 1.40 g of 2-chlorobenz-S-methylisothioamide hydroiodide was obtained. Yield, 85%; m.p., 127–130° C.

EXAMPLE 15

First, 1.30 g of (4'-methyl-1,1'-biphen-2-yl)-S-methylisothioamidehydroiodide was dissolved in 4 ml of methanol, and a solution of 0.12 g of anhydrous hydrazine dissolved in 1 ml of methanol was added for 30 minutes. At 0° C. to room temperature, stirring was continued overnight, and about 50 ml of ether was added. The reaction mixture was filtered at 0° C. to give 1.25 g of (4'-methyl-1,1'-biphen-2-yl)-amidrazone hydroiodide. Yield, 96%; m.p., 140–144° C. (decomp.)

EXAMPLE 16

The procedure in Example 15 was repeated in the same manner as described in Example 15, except that 2-chlorobenz-S-methylisothioamide hydroiodide was used in place of (4'-methyl-1,1'-biphen-2-yl)-S-methylisothioamide hydroiodide, and (2-chlorobenz)amidrazone was obtained. Yield, 93%

EXAMPLE 17

First, 2.08 g (4.11 mmol) of [8-[4-(4-phenylbutoxy)benzoyl]amino-4-oxo-4H-benzopyran-2-yl]amidrazone was dissolved in 180 g of acetic acid, and 60 g of water and 0.42 g (6.17 mmol) of sodium nitrite were added thereto, followed by stirring at 0–2° C. for 2 hours. After the completion of the reaction was checked, the reaction mixture was filtered to give 8-[4-(4-phenylbutoxy)benzoyl]amino-2-(tetrazol-5-yl)4-oxo4H-benzopyran. Product amount, 1.97 g; yield, 96%

EXAMPLES 18–20

The reaction in Example 17 was effected in the same manner as described in Example 17, except that the starting materials shown in Table 3 were used in place of [8-[4-(4-phenylbutoxy)benzoyl]amino-4-oxo-4H-benzopyran-2-yl]amidrazone, and the corresponding tetrazole compounds were obtained.

TABLE 3

| Example | Starting Material Name |
| --- | --- |
| 18 | 2-(6-Chloro-4-oxo-4H-benzopyran-2-yl)amidrazone |
| 19 | 2-Chlorobenzamidrazone |
| 20 | (4'-Methyl-1,1'-biphenyl-2-yl)amidrazone hydroiodide |

| Example | Product |
| --- | --- |
| 18 | 6-Chloro-2-(tetrazol-5-yl)-4-oxo-4H-benzopyran<br>Yield, 93% |
| 19 | 5-(2-Chlorophenyl)tetrazol<br>Yield, 80% |
| 20 | 2-(Tetrazol-5-yl)-4'-methyl-1,1'-biphenyl<br>Yield, 86% |

EXAMPLE 21

First, 71.2 mmol of 2-chlorobenzonitrile was dissolved in 50 ml of methanol, and 356 mmol of hydrazine and 35.6 mmol of 28% methylate were added thereto, followed by keeping at the reflux temperature for 5 hours. The reaction mixture was concentrated under reduced pressure. The residue was dissolved in 50 ml of 50% hydrochloric acid, and 74.8 mmol of sodium nitrite was added thereto at 0C to cause reaction. The reaction mixture was extracted with ethyl acetate to give 5-(2-chlorophenyl)tetrazole. Yield, 70%.

EXAMPLE 22

First, 26.9 mmol of 2-cyano-4'-methyl-1,1'-biphenyl was dissolved in 150 ml of ethanol, and 270 mmol of hydrazine and 77.7 nmuol of 28% methylate were added thereto, followed by keeping at 50° C. for 48 hours. The reaction mixture was concentrated under reduced pressure. The residue was dissolved in 100 ml of ethanol, and 55 mmol of sodium nitrite and 110 mmol of concentrated hydrochloric acid were added to the solution at 0° C. After keeping at 0–5° C. for 2 hours, the reaction mixture was concentrated to give 2-(tetrazol-5-yl)-4'-methyl-1, I'-biphenyl. Yield, 46%

EXAMPLE 23

First, 35.6 mmol of 2-chlorobenzonitrile was dissolved in 50 ml of methanol, and 35.6 mmol of triethylamine and 105 mmol of hydrogen sulfide were added thereto at room temperature, followed by adding 180 mmol of anhydrous hydrazine and keeping at the reflux temperature for 48 hours. The reaction mixture was evaporated under reduced pressure. The residue was dissolved in 50 ml of 5% hydrochloric acid, and 75 mmol of sodium nitrite was added thereto at 0° C. to cause reaction. After completion of the reaction, the reaction mixture was extracted with ethyl acetate to give 5-(2-chlorophenyl)tetrazole. Yield, 54%

EXAMPLES 24–27

The use of 2-bromobenzonitrile, 3-bromobenzonitrile, 2-nitrobenzonitrile or 3-nitrobenzonitrile in place of 2-chlorobenzonitrile in Example 21 or 23 makes it possible to obtain the corresponding tetrazole compound: 5-(2-bromophenyl)tetrazole, 5-(3-bromophenyl)tetrazole, 5-(2-nitrophenyl)tetrazole or 5-(3-nitrophenyl)tetrazole.

EXAMPLE 28

First, 26.9 mmol of 2-cyano-4'-methyl-1,1'-biphenyl was dissolved in 150 ml of ethanol, and 53.9 mmol of triethylamine and 105 mmol of hydrogen sulfide were added to the solution at room temperature, followed by adding 134.5 mmol of anhydrous hydrazine and keeping at the reflux temperature for 48 hours. The reaction mixture was warmed. The reaction mixture was concentrated under reduced pressure. The residue was dissolved in 100 ml of ethanol added thereto, and 108 mmol of sodium nitrite and 100 ml of concentrated hydrochloric acid was added at 0C. After keeping at 0–5° C. for 2 hours, the reaction mixture was extracted with ethyl acetate to give 2-(tetrazol-5-yl)-4'-methyl-1,1'-biphenyl. Yield, 52%

EXAMPLES 29–31

The use of 2-cyano-1,1'-biphenyl, 2-cyano-4'-chloromethyl-1,1'-biphenyl or 2-cyano-4'-methoxymethyl-1,1'-biphenyl in place of 2-cyano4'-methyl-1,1'-biphenyl in Example 28 makes it possible to obtain the corresponding compound: 2-(tetrazol-5-yl)-1,1'-biphenyl, 2-(tetrazol-5-yl)-4'-chloromethyl-1,1'-biphenyl or 2-(tetrazol-5-yl)4'-methoxymethyl-1,1'-biphenyl.

EXAMPLE 32

(1) Into a mixture of 4.13 g (30 mmol) of 2-chlorobenzonitrile, 30 g of ethanol, 1.10 g (15 mmol) of diethylamine and 1.92 g (60 mmol) of anhydrous hydrazine was bubled 0.67 g (19.7 mmol) of hydrogen sulfide gas at room temperature, followed by stirring at 60° C. for 24 hours. The resulting reaction mixture was concentrated and dried to give 3.22 g of 2-chlorobenzamidrazone (63% yield).

(2) First, 569 mg (3.35 mmol) of 2-chlorobenzamidrazone produced according to (1) was dissolved in 15 g of N,N-dimethylformamide and 10.5 g (14.4 mmol) of 5% hydrochloric acid, followed by cooling to 5° C. Then, 2.96 g (4.29 mmol) of aqueous sodium nitrite was added dropwise thereto, followed by stirring at 0–5° C. for 4 hours. The resulting reaction mixture was analyzed by liquid chromatography with an internal standard, and it was found that 583 mg (3.23 mmol, 96% yield) of 5-(2-chlorophenyl)tetrazole was contained.

The reaction mixture was concentrated to remove the solvent, and 40 g of 4% aqueous sodium hydroxide and 30 ml of toluene were added to perform an extraction and phase separation. The resulting aqueous layer was further washed twice with 30 ml of toluene and adjusted to pH 1 or lower by the addition of 36% hydrochloric acid The deposited solid was filtered and dried to give 508 mg (99.2% purity) of 5-(2-chlorophenyl)tetrazole.

EXAMPLE 33

Into a mixture of 4.13 g (30 mmol) of 2-chlorobenzonitrile, 30 g of ethanol, 1.10 g (15mmol) of diethylamine and 1.92 g (60 mmol) of anhydrous hydrazine was bubbled 0.62 g (18.2 mmol) of hydrogen sulfide gas at room temperature, followed by stirring at 60° C. for 9.5 hours. The resulting reaction mixture was concentrated, dried and dissolved in 120 g of N,N-dimethylformamide and 54.7 g (150 mmol) of 10% hydrochloric acid added thereto, followed by cooling to 5° C. Then 20.7 g (60 mmol) of 20% sodium nitrite was added dropwise thereto, followed by stirring at 0–5° C. for 3 hours. The resulting reaction mixture was filtered to remove undissolved matters. The filtrate was analyzed by liquid chromatography with an internal standard, and it was found that 3.76 g (20.8 mmol, 69% yield) of 5-(2-chlorophenyl)tetrazole was contained.

The filtrate was concentrated to remove the solvent, followed by the same work up as described in Example 32, (2) to give 3.36 g (96.4% purity) of 5-(2-chlorophenyl) tetrazole.

EXAMPLE 34

Into a mixture of 5.0 g (27.5 mmol) of 2-bromobenzonitrile, 30 g of ethanol, 1.10 g (15 mmol) of diethylamine and 1.76 g (55 mmol) of anhydrous hydrazine was bubbled 0.58 g (17 mmol) of hydrogen sulfide gas at room temperature, followed by stirring at 60° C. for 22 hours. The resulting reaction mixture was concentrated, dried and dissolved in 110 g of N,N-dimethylformamide and 50.3 g (138 mmol) of 10% hydrochloric acid added thereto, followed by cooling to 5° C. Then, 19.0 g (55 mmol) of 20% sodium nitrite was added dropwise thereto, followed by stirring at 0–5° C. for 2 hours. The resulting reaction mixture was filtered to remove undissolved matters. The filtrate was analyzed by liquid chromatography with an internal standard, and it was found that 4.88 g (21.7 mmol, 79% yield) of 5-(2-bromophenyl)tetrazole was contained.

The filtrate was concentrated to remove the solvent, followed by the same work up as described in Example 32, (2) to give 4.75 g (93.1% purity) of 5-(2-bromophenyl) tetrazole.

What is claimed is:

1. A process for producing a tetrazole compound of general formula (1):

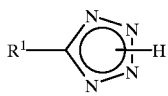 (1)

wherein $R^1$ is as defined below, characterized in that a nitrile of general formula (2):

$R^1CN$ (2)

wherein $R^1$ is a 4-oxo-4H-benzopyranyl group substituted with $R^2$, or a phenyl group substituted in its 2-position with X, in which $R^2$ is an $R^3CONH$ group; $R^3$ is a $C_1$–$C_{20}$ alkyl group, a phenyl group, a phenyl-substituted ($C_1$–$C_{20}$) alkyl group, a phenyl-substituted ($C_1$–$C_{20}$) alkoxyphenyl group or a ($C_1$–$C_{20}$) alkoxyphenyl group; X is a phenyl group optionally substituted with Y; and Y is a $C_1$–$C_{20}$ alkyl group, a $C_1$–$C_{20}$ alkyl group substituted with one or more hydroxy groups whereby optionally the hydrogen atom in the hydroxy group is replaced for protection, a $C_1$–$C_{20}$ alkyl group substituted with one or more amino groups whereby optionally at least one hydrogen atom in the amino group is replaced for protection, a $C_1$–$C_{20}$ alkyl group with at least one hydrogen atom being replaced by a halogen atom, a $C_1$–$C_{20}$ alkoxy group, a $C_1$–$C_{20}$ alkoxy group substituted with one or more hydroxy groups whereby optionally at least one of the hydrogen atom(s) in the hydroxy group(s) is replaced for protection, a $C_1$–$C_{20}$ alkoxy group substituted with one or more amino groups whereby optionally at least one hydrogen atom in the amino group is replaced for protection, or a $C_1$–$C_{20}$ alkoxy group with at least one hydrogen atom being replaced by a halogen atom, is reacted with anhydrous hydrazine or a salt thereof in the presence of a catalyst which is at least one selected from alkoxides, alkali metals, alkali metal amides, alkali metal hydrides, alkaline earth metal hydrides, sulfides or salts thereof, thiocyanoates, pyridine compounds, alkylamines, aromatic amines, diamines and organic quarternary ammonium salts, followed by reaction with a nitrous acid compound of general formula (3):

$ANO_2$ (3)

wherein A is a hydrogen atom, an alkali metal, an alkaline earth metal or a $C_1$–$C_{20}$ alkyl group.

2. The production process according to claim 1, wherein $R^1$ is a 4-oxo-4H-benzopyranyl group optionally substituted with $R^2$.

3. The production process according to claim 1, wherein X is a phenyl group or a ($C_1$–$C_{20}$) alkylphenyl group.

4. The production process according to claim 1, wherein the catalyst is a sulfide or a salt thereof, an alkylamine, a mixture of a sulfide or a salt thereof and an alkylamine, or an alkoxide.

5. The production process according to claim 1, wherein the catalyst is hydrogen sulfide or a salt thereof, or a mixture of hydrogen sulfide or a salt thereof and an alkylamine.

6. The production process according to claim 1, wherein $R^1$ is a phenyl group or a phenyl group substituted with X, and X is a halogen atom.

7. The production process according to claim 2, wherein the catalyst is used at an amount of from 0.001 mole inclusive to 1 mole exclusive, relative to nitrile (2).

8. The production process according to claim 6, wherein the catalyst is used at an amount of from 0.001 mole inclusive to 1 mole exclusive, relative to nitrile (2).

9. The process according to claim 1, wherein the anhydrous hydrazine is added to the nitrile at about 0° C. to form a reaction mixture.

10. The production process according to claim 1, wherein the nitrile of general formula (2) is reacted with anhydrous hydrazine.

* * * * *

UNITED STATES PATENT AND TRADEMARK OFFICE
CERTIFICATE OF CORRECTION

PATENT NO. : 6,191,289 B1  Page 1 of 1
APPLICATION NO. : 09/176198
DATED : February 20, 2001
INVENTOR(S) : Hideki Ushio et al.

It is certified that error appears in the above-identified patent and that said Letters Patent is hereby corrected as shown below:

On title page
Please correct category [30] Foreign Application Priority Data as follows:

Item -- [30] Foreign Application Priority Data

May 16, 1994   [JP] Japan ..................... 6-100832
    March 28, 1995  [JP] Japan ..................... 7-069204 --

Signed and Sealed this

Twenty-fifth Day of December, 2007

JON W. DUDAS
*Director of the United States Patent and Trademark Office*